US010758111B2

(12) United States Patent
Valdastri et al.

(10) Patent No.: US 10,758,111 B2
(45) Date of Patent: Sep. 1, 2020

(54) HYDRO-JET ENDOSCOPIC CAPSULE AND METHODS FOR GASTRIC CANCER SCREENING IN LOW RESOURCE SETTINGS

(71) Applicant: Vanderbilt University, Nashville, TN (US)

(72) Inventors: Pietro Valdastri, Nashville, TN (US); Keith Obstein, Nashville, TN (US); Robert Caprara, Nashville, TN (US); Christopher Lyne, Nashville, TN (US); Federico Campisano, Nashville, TN (US); Gabrielmaria Scozzarro, Nashville, TN (US); Alexander Vartanian, Nashville, TN (US); William Jones, Nashville, TN (US); Christian Di Natali, Nashville, TN (US); Marco Beccani, Nashville, TN (US); Erdem Erdemir, Nashville, TN (US); Douglas R. Morgan, Nashville, TN (US)

(73) Assignee: Vanderbilt University, Nashville, TN (US)

( * ) Notice: Subject to any disclaimer, the term of this patent is extended or adjusted under 35 U.S.C. 154(b) by 447 days.

(21) Appl. No.: 15/509,793

(22) PCT Filed: Sep. 9, 2015

(86) PCT No.: PCT/US2015/049142
§ 371 (c)(1),
(2) Date: Mar. 8, 2017

(87) PCT Pub. No.: WO2016/040451
PCT Pub. Date: Mar. 17, 2016

(65) Prior Publication Data
US 2017/0245741 A1 Aug. 31, 2017

Related U.S. Application Data

(60) Provisional application No. 62/048,105, filed on Sep. 9, 2014.

(51) Int. Cl.
*A61B 1/04* (2006.01)
*A61B 1/00* (2006.01)
(Continued)

(52) U.S. Cl.
CPC .......... *A61B 1/041* (2013.01); *A61B 1/00156* (2013.01); *A61B 1/01* (2013.01); *A61B 1/015* (2013.01); *A61B 2562/0219* (2013.01)

(58) Field of Classification Search
CPC ............... A61M 25/0122; A61B 1/041; A61B 1/00156; A61B 1/01; A61B 1/015; A61B 2562/0219
(Continued)

(56) References Cited

U.S. PATENT DOCUMENTS 3,315,660 A  4/1967 Abella
3,858,572 A  1/1975 Binard et al.
(Continued)

FOREIGN PATENT DOCUMENTS

CN  101778592 A  7/2010
DE  102006019419  11/2007
(Continued)

OTHER PUBLICATIONS

Althoefer et al., "Air-cushion force sensitive probe for soft tissue investigation during minimally invasive surgery," 2008, pp. 827-830.
(Continued)

*Primary Examiner* — Anh Tuan T Nguyen
*Assistant Examiner* — Shankar Raj Ghimire
(74) *Attorney, Agent, or Firm* — Michael Best & Friedrich LLP

(57) ABSTRACT

Systems and methods are provided for controlling lateral movement of a medical capsule system. A capsule housing is configured to be inserted into an anatomical structure of a patient. The multichannel tether is coupled to a rear of the capsule and includes at least one liquid exhaust channel conveying liquid to the capsule housing. The plurality of liquid exhaust ports are positioned around an outer circumference of the capsule housing and each configured to controllably expel liquid laterally from the capsule housing at varying rates to affect lateral movement of the capsule housing.

20 Claims, 7 Drawing Sheets

(51) Int. Cl.
  *A61B 1/01* (2006.01)
  *A61B 1/015* (2006.01)

(58) Field of Classification Search
  USPC ........................................ 604/95.02
  See application file for complete search history.

(56) References Cited

U.S. PATENT DOCUMENTS

| | | | |
|---|---|---|---|
| 3,870,072 A | 3/1975 | Lindemann | |
| 4,048,992 A | 9/1977 | Lindemann et al. | |
| 4,207,887 A | 6/1980 | Hiltebrandt et al. | |
| 4,287,809 A | 9/1981 | Egli et al. | |
| 4,314,251 A | 2/1982 | Raab | |
| 4,769,006 A * | 9/1988 | Papantonakos | A61B 1/00156 600/485 |
| 4,991,957 A * | 2/1991 | Sakamoto | A61B 1/0005 356/241.4 |
| 5,330,486 A | 7/1994 | Wilk | |
| 5,489,256 A * | 2/1996 | Adair | A61B 1/00073 600/123 |
| 6,248,080 B1 | 6/2001 | Miesel et al. | |
| 6,270,787 B1 | 8/2001 | Ayer | |
| 6,802,811 B1 | 10/2004 | Slepian | |
| 7,647,090 B1 * | 1/2010 | Frisch | A61B 1/00105 600/109 |
| 7,722,559 B2 | 5/2010 | Uesugi et al. | |
| 8,652,102 B2 * | 2/2014 | Nitsan | A61M 3/0283 604/150 |
| 2001/0051766 A1 | 12/2001 | Gazdzinski | |
| 2002/0065455 A1 | 5/2002 | Ben-Haim et al. | |
| 2003/0114731 A1 | 6/2003 | Cadeddu et al. | |
| 2003/0214579 A1 * | 11/2003 | Iddan | A61B 1/00156 348/81 |
| 2003/0214580 A1 | 11/2003 | Iddan | |
| 2005/0124928 A1 * | 6/2005 | Beck | A61B 17/22012 604/43 |
| 2005/0154277 A1 * | 7/2005 | Tang | A61B 1/00016 600/407 |
| 2005/0267334 A1 * | 12/2005 | Swain | A61B 1/00091 600/156 |
| 2005/0277852 A1 | 12/2005 | Shih et al. | |
| 2006/0004276 A1 * | 1/2006 | Iddan | A61B 1/00156 600/407 |
| 2006/0188407 A1 * | 8/2006 | Gable | A61B 5/0084 604/19 |
| 2007/0015968 A1 * | 1/2007 | Shelnutt | A61B 1/00156 600/156 |
| 2007/0221233 A1 | 9/2007 | Kawano | |
| 2008/0015413 A1 * | 1/2008 | Barlow | A61B 1/00105 600/114 |
| 2008/0021334 A1 | 1/2008 | Finburgh et al. | |
| 2008/0058835 A1 | 3/2008 | Farritor et al. | |
| 2008/0154093 A1 * | 6/2008 | Cho | A61B 1/00147 600/114 |
| 2008/0207999 A1 | 8/2008 | Abraham-Fuchs et al. | |
| 2008/0300453 A1 * | 12/2008 | Aoki | A61B 1/00156 600/103 |
| 2008/0300458 A1 | 12/2008 | Kim et al. | |
| 2009/0024142 A1 | 1/2009 | Ruiz Morales | |
| 2009/0054877 A1 | 2/2009 | Hood et al. | |
| 2009/0054909 A1 | 2/2009 | Farritor et al. | |
| 2009/0171268 A1 | 7/2009 | Williams, Jr. et al. | |
| 2009/0171373 A1 | 7/2009 | Farritor et al. | |
| 2009/0182197 A1 * | 7/2009 | Goldwasser | A61B 1/00082 600/115 |
| 2009/0292205 A1 | 11/2009 | Osaka | |
| 2010/0049120 A1 * | 2/2010 | Dijksman | A61B 1/041 604/66 |
| 2010/0100117 A1 | 4/2010 | Brister et al. | |
| 2010/0198008 A1 * | 8/2010 | Kawano | A61B 1/00158 600/109 |
| 2010/0256636 A1 | 10/2010 | Fernandez et al. | |
| 2011/0184235 A1 | 7/2011 | Schostek et al. | |
| 2011/0202070 A1 | 8/2011 | Dario et al. | |
| 2011/0301497 A1 | 12/2011 | Shachar et al. | |
| 2011/0313415 A1 | 12/2011 | Fernandez et al. | |
| 2012/0035416 A1 | 2/2012 | Fernandez et al. | |
| 2012/0041345 A1 | 2/2012 | Rajamani et al. | |
| 2012/0149981 A1 | 6/2012 | Khait et al. | |
| 2012/0232362 A1 * | 9/2012 | Gable | A61B 5/150755 600/310 |
| 2012/0238796 A1 | 9/2012 | Conlon | |
| 2012/0253284 A1 * | 10/2012 | Nitsan | A61M 3/0283 604/150 |
| 2012/0271555 A1 | 10/2012 | Levental et al. | |
| 2013/0018224 A1 * | 1/2013 | Kim | A61B 1/00156 600/109 |
| 2013/0131695 A1 | 5/2013 | Scarfogliero et al. | |
| 2013/0165859 A1 | 6/2013 | Imran | |
| 2013/0225922 A1 | 8/2013 | Schentag et al. | |
| 2013/0245356 A1 | 9/2013 | Fernandez et al. | |
| 2013/0298715 A1 | 11/2013 | Valdastri et al. | |
| 2013/0324914 A1 | 12/2013 | Valdastri et al. | |
| 2014/0081120 A1 | 3/2014 | Valdastri et al. | |
| 2014/0081169 A1 | 3/2014 | Gerding et al. | |
| 2014/0206953 A1 | 7/2014 | Valdastri et al. | |
| 2014/0206956 A1 * | 7/2014 | Rabinovitz | G01N 33/54386 600/302 |
| 2014/0249372 A1 * | 9/2014 | Yoshida | A61B 1/00091 600/121 |
| 2014/0358162 A1 | 12/2014 | Valdastri et al. | |
| 2015/0045725 A1 | 2/2015 | Smith et al. | |
| 2015/0342501 A1 | 12/2015 | Di Natali et al. | |

FOREIGN PATENT DOCUMENTS

| | | | |
|---|---|---|---|
| EP | 2163206 | 3/2010 | |
| EP | 2286756 | 2/2011 | |
| JP | H04144533 A | 5/1992 | |
| WO | 9405200 A1 | 3/1994 | |
| WO | 2000030548 | 6/2000 | |
| WO | 2004041068 | 5/2004 | |
| WO | WO-2004041068 A2 * | 5/2004 | ......... A61B 1/00156 |
| WO | WO-2006045011 A2 * | 4/2006 | ......... A61B 1/00156 |
| WO | 2007013059 | 2/2007 | |
| WO | 2007146987 | 12/2007 | |
| WO | 2008016196 A1 | 2/2008 | |
| WO | WO-2008016196 A1 * | 2/2008 | ......... A61B 1/00156 |
| WO | 2008122997 | 10/2008 | |
| WO | 2009014917 | 1/2009 | |
| WO | 2010042611 | 4/2010 | |
| WO | 2010042611 A1 | 4/2010 | |
| WO | 2010044053 | 4/2010 | |
| WO | 2010046823 | 4/2010 | |
| WO | 2011058505 | 5/2011 | |
| WO | 2011135503 | 11/2011 | |
| WO | 2012028557 | 3/2012 | |
| WO | 2012035157 | 3/2012 | |

(56) References Cited

FOREIGN PATENT DOCUMENTS

| WO | 2012080947 | 6/2012 |
|---|---|---|
| WO | 2012164517 | 12/2012 |
| WO | 2013027182 | 2/2013 |

OTHER PUBLICATIONS

American Cancer Society, "What are the key statistics about colorectal cancer?" http://www.cancer.org/Cancer/ColonandRectumOancer/DetailedGuide/colorectal-cancer-key-statistics. Jun. 2012.

Arber et al., Proof-of-concept study of the aer-o-scope omnidirectional colonoscopic viewing system in ex vivo and in vivo porcine models. Endoscopy, 39(5):412-417, May 2007.

Bajo et al., "Configuration and Joint Space Feedback for Improved Accuracy of Continuum Robots," in IEEE International Conference on Robotics and Automation, 2011, pp. 2905-2912.

Bajo et al., "Finding Lost Wrenches: Using Continuum Robots for Contact Detection and Estimation of Contact Location," in 2010 IEEE International Conference on Robotics and Automation, 2010, pp. 3666-3673.

Bajo et al., "Integration and Preliminary Evaluation of an Insertable Robotic Effectors Plafform for Single Port Access Surgery," IEEE International Conference on Robotics and Automation, Saint Paul, MN, 2012, pp. 3381-3387.

Bajo et al., "Kinematics-Based Detection and Localization of Contacts Along Multisegment Continuum Robots," IEEE Transactions on Robotics, 2012; 28(2): 291-302.

Bhattacharyya, "Motion Planning and Constraint Exploration for Robotic Surgery," M.Sc. thesis, (Advisor: N. Simaan), Mechanical Engineering, Vanderbilt University, 2011; 1-130.

Burgner et al., "A bimanual teleoperated system for endonasal skull base surgery," in 2011 IEEE/RSJ International Conference on Intelligent Robots and Systems, 2011, pp. 2517-2523.

Burling et al., Automated Insufflation of Carbon Dioxide for MDCT Colonography: Distension and Patient Experience Compared with Manual Insufflation. Journal of Radiology, 2006; 186: 96-103.

Castanheira et al., "Fluorescence and diffuse reflectance spectroscopy for early cancer detection using a new strategy towards the development of a miniaturized system," IEEE Engineering in Medicine and Biology Society. Conference. 2010. 1210-3.

Ciuti, "Innovative control platforms for robotic microsystems in endoluminal surgery," Master's thesis, Scuola Superiore di Studi Universitari e Perfezionamento Sant' Anna, 2012.

Conway et al., "Endoscopic hemostatic devices," Gastrointest Endosc. 2009; 69(6):987-96.

Culmer et al., "Reviewing the technological challenges associated with the development of a laparoscopic palpation device," The International Journal of Medical Robotics and Computer Assisted Surgery, vol. 8, No. 2, pp. 146-159, 2012.

Dario et al., "An advanced robot system for automated diagnostic tasks through palpation," IEEE Trans. Biomed. Eng., vol. 35, No. 2, pp. 118-126, 1988.

Davila et al., Asge guideline: colorectal cancer screening and surveillance, American Society for Gastrointestinal Endoscopy, 2006; 63(4): 546-557.

Dellon et al., "The use of carbon dioxide for insufflation during GI endoscopy: a systematic review Gastrointestinal Endoscopy," 69:843-849, 2009.

Dietzel et al., "Magnetic active agent release system (maars): Evaluation of a new way for a reproducible, externally controlled drug release into the small intestine," J Control Release. Aug. 10, 2012;161(3):722-7.

Dupont et al., "Design and Control of Concentric-Tube Robots.," IEEE transactions on robotics : a publication of the IEEE Robotics and Automation Society, vol. 26, No. 2, pp. 209-225, Apr. 2010.

Edwards et al., Annual report to the nation on the status of cancer, 1975-2006, featuring colorectal cancer trends and impact of interventions (risk factors, screening, and treatment) to reduce future rates. Cancer, pp. 544-574, 2010.

Egorov et al., "Mechanical Imaging of the Breast," vol. 27, No. 9, pp. 1275-1287, 2008.

Egorov et al., "Prostate mechanical imaging: 3-D image composition and feature calculations," vol. 25, No. 10, pp. 1329-1340, 2006.

Faigel, Endoscopic Oncology: Gastrointestinal Endoscopy and Cancer Management. Humana Press, 2006.

Fleming et al., The safety of helim for abdominal insufflation. Surgical Endoscopy, 11:230-234 230-234, 1997.

Fuller et al., "Laparoscopic trocar injuries: A report from a U.S. Food and Drug Administration (FDA) Center for Devices and Radiological Health (CDRH) Systematic Technology Assessment of Medical Products (STAMP) committee," 2003, www.fda.gov/medicaldevices/safety/alertsandnotices/ucm197339.htm.

Furlani, Permanent Magnet and Electromechanical Devices. Academic Press, 2001, pp. 131-135.

Goldman et al., "Algorithms for autonomous exploration and estimation in compliant environments," Robotica, 2012; 1-17.

Goldman et al., "Analysis , Algorithms , and Control for Intelligent Surgical Exploration and Intervention," Ph.D. Dissertation, (Advisor: N. Simaan), Mechanical Engineering, Columbia University, 2011; 1-148.

Goldman et al., "Compliant Motion Control for Continuum Robots with Intrinsic Actuation Sensing," in IEEE International Conference on Robotics and Automation, 2011, pp. 1126-1132.

Goldman et al., "Design and Performance Evaluation of a Minimally Invasive Telerobotic Platform for Transurethral Exploration and Intervention," ASME Journal on Medical Devices, vol. submitted, pp. 1-27, 2011.

Gossum et al., Capsule endoscopy versus colonoscopy for the detection of polyps and cancer. N Engl J Med, 361(3):264-270, Jul. 2009.

Gwilliam et al., "Human vs. robotic tactile sensing: Detecting lumps in soft tissue," in IEEE Haptics Symposium, 2010, pp. 21-28.

Howe et al., "Remote palpation technology," IEEE Eng. Med. Biol. Mag., vol. 14, No. 3, pp. 318-323, 1995.

Inadomi et al., Adherence to colorectal cancer screening: A randomized clinical trial of competing strategies. Archives of Internal Medicine, 172(7):575-582, 2012.

Intuitive Surgical website: www.intuitivesurgical.com.

Kapoor et al., "Suturing in Confined Spaces: Constrained Motion Control of a Hybrid 8-DoF Robot", in IEEE International Conference on Advanced Robotics, 2005.

Kapoor et al., "Telemanipulation of Snake-Like Robots for Minimally Invasive Surgery of the Upper Airway," in MICCAI 2006 workshop on medical robotics, 2006.

Kong et al., "A rotational micro biopsy device for the capsule endoscope," Intelligent robots and systems. In Intelligent Robots and Systems, 2005; 1839-1843.

Kubler et al., "Development of actuated and sensor integrated forceps for minimally invasive robotic surgery," The International Journal of Medical Robotics and Computer Assisted Surgery, vol. 1, No. 3, pp. 96-107, 2005.

Kucuk et al., "Chapter 4. Robot Kinematics: Forward and Invers Kinematics," Industrial Robotics; Theory, Modeling and Control, textbook edited by Sam Cubero, published 2006, by Pro Literatur, Germany.

Kunkel et al., "Using robotic systems in order to determine biomechanical properties of soft tissues," in Studies in Health Technology and Informatics, Proceedings of the 2nd Conference on Applied Biomechanics, vol. 133, No. 3, 2008, p. 156.

Lederman et al., "Force variability during surface contact with bare finger or rigid probe," 12th International Symposium on Haptic Interfaces for Virtual Environment and Teleoperator Systems, 2004. HAPTICS '04. Proceedings., pp. 154-160, 2004.

Leung et al., "Impact of a novel water method on scheduled unsedated colonoscopy in U.S. veterans," Gastrointestinal Endoscopy, 69(3, Part 1):546-550, 2009.

Li et al.,"Diagnostic value of fecal tumor m2-pyruvate kinase for cm screening: a systematic review and meta-analysis," Int J Cancer Oct. 15, 2012;131(8):1837-45.

Lister et al., "Development of in vivo constitutive models for liver: Application to surgical simulation," Annals of Biomedical Engineering, vol. 39, pp. 1060-1073, 2011.

(56) References Cited

OTHER PUBLICATIONS

Liu et al., "A haptic probe for soft tissue abnormality identification during minimally invasive surgery," 2009, pp. 117-422.

Liu et al., "Experimental study of soft tissue recovery using optical fiber probe," 2007, pp. 516-521.

Liu et al., "Rolling indentation probe for tissue abnormality identification during minimally invasive surgery," IEEE Trans. Robot, vol. 27, No. 3, pp. 450-460, 2011.

Liu et al., "Rolling Mechanical Imaging: A Novel Approach for Soft Tissue Modeling and Identification during Minimally Invasive Surgery," 2008, pp. 845-849.

J. Ferlay, I. Soerjomataram, M. Ervik, R. Dikshit, S. Eser, C. Mathers, M. Rebelo, D. M. Parkin, D. Forman, and F. Bray, "Globocan 2012, Cancer Incidence and Mortality Worldwide: IARC CancerBase," 2013.

American Cancer Society, "Cancer Facts & Figures 2005," 2005.

F. Bray, A. Jemal, N. Grey, J. Ferlay, and D. Forman, "Global Cancer Transitions According to the Human Development Index: A Population-Based Study," The Lancet Oncology, vol. 13, pp. 790-801, 2012.

H.-O. Adami, N. E. Day, D. Trichopoulos, and W. Willett, "Primary and Secondary Prevention in the Reduction of Cancer Morbidity and Mortality." Eur. J. Cancer, vol. 37 Suppl 8, pp. S118-S127, 2001.

K.-J. Lee, M. Inoue, T. Otani, M. Iwasaki, S. Sasazuki, and S. Tsugane, "Gastric Cancer Screening and Subsequent Risk of Gastric Cancer: A Large-Scale Population-Based Cohort Study, with a 13-Year Follow-Up in Japan," Int. J. Cancer, vol. 118, No. 9, pp. 2315-2321, May 2006.

H. Makuuchi, T. Machimura, H. Shimada, K. Mizutani, O. Chino, Y. Kise, T. Nishi, H. Tanaka, T. Mitomi, M. Horiuchi, M. Sakai, J. Gotoh, J. Sasaki, and Y. Osamura, "Endoscopic Screening for Esophageal Cancer in 788 Patients with Head and Neck Cancers," The Tokai Journal of Experimental and Clinical Medicine, vol. 21, pp. 139-145, 1996.

A. Oshima, N. Hirata, T. Ubukata, K. Umeda, and I. Fujimoto, "Evaluation of a Mass Screening Program for Stomach Cancer with a Casecontrol Study Design," Int. J. Cancer, vol. 38, No. 6, pp. 829-833, Dec. 1986.

T. J. Wilhelm, H. Mothes, D. Chiwewe, B. Mwatibu, and G. Kahler, "Gastrointestinal Endoscopy in a Low Budget Context: Delegating EGD to Non-Physician Clinicians in Malawi can be Feasible and Safe." Endoscopy, vol. 44, No. 2, pp. 174-176, Feb. 2012.

A. Koulaouzidis and S. Douglas, "Capsule Endoscopy in Clinical Practice: Concise Up-To-Date Overview." Clinical and Experimental Gastroenterology, vol. 2, pp. 111-116, Jan. 2009.

J. F. Rey, H. Ogata, N. Hosoe, K. Ohtsuka, N. Ogata, K. Ikeda, H. Aihara, I. Pangtay, T. Hibi, S. Kudo, and H. Tajiri, "Feasibility of Stomach Exploration with a Guided Capsule Endoscopy," Endoscopy, vol. 42, No. 7, pp. 541-545, Jul. 2010.

D. S. Mishkin, R. Chuttani, J. Croftle, J. Disario, J. Liu, R. Shah, L. Somogyi, W. Tierney, L. M. W. K. Song, and B. T. Petersen, "ASGE Technology Status Evaluation Report: Wireless Capsule Endoscopy." Gastrointestinal Endoscopy, vol. 63, No. 4, pp. 539-545, Apr. 2006.

H. Keller, A. Juloski, H. Kawano, M. Bechtold, A. Kimura, H. Takizawa, and R. Kuth, "Method for Navigation and Control of a Magnetically Guided Capsule Endoscope in the Human Stomach," Proc. of the IEEE RAS and EMBS Int. Conf. on Biomedical Robotics and Biomechatronics, pp. 859-865, 2012.

S. Yim and M. Sitti, "Design and Analysis of a Magnetically Actuated and Compliant Capsule Endoscopic Robot," 2011 IEEE Int. Conf. Robot. Autom., pp. 4810-4815, May 2011.

S. Yim, K. Goyal, and M. Sitti, "Magnetically Actuated Soft Capsule With the Multimodal Drug Release Function," IEEE/ASME Trans. Mechatronics, vol. 18, No. 4, pp. 1413-1418, 2013.

S. Yim, E. Gultepe, D. H. Gracias, and M. Sitti, "Biopsy Using a Magnetic Capsule Endoscope Carrying, Releasing, and Retrieving Untethered Microgrippers." IEEE Trans. Biomed. Eng., vol. 61, No. 2, pp. 513-521, Feb. 2014.

G. Tortora, P. Valdastri, E. Susilo, A. Menciassi, P. Dario, F. Rieber, and M. O. Schurr, "Propeller-Based Wireless Device for Active Capsular Endoscopy in the Gastric District," Minimally Invasive Therapy & Allied Technologies, vol. 18, pp. 280-290, 2009.

De Falco, G. G Tortora, P. Dario, and A. Menciassi, "An Integrated System for Wireless Capsule Endoscopy in a Liquid-Distended Stomach," IEEE Trans. Biomed. Eng., vol. 61, No. 3, pp. 794-804, Mar. 2013.

M. Simi, N. N Tolou, P. Valdastri, J. L. Herder, A. Menciassi, P. Dario, "Modeling of a Compliant Joint in a Magnetic Levitation System for an Endoscopic Camera", Mechanical Sciences, 2012, vol. 3, pp. 5-14.

Varadarajulu, S. Banerjee, B. A. Barth, D. J. Desilets, V. Kaul, S. R. Kethu, M. C. Pedrosa, P. R. Pfau, J. L. Tokar, A. Wang, L. M. Wong Kee Song, and S. A. Rodriguez, "GI Endoscopes," Gastrointestinal Endoscopy, vol. 74, No. 1, pp. 1-6.e6, Jul. 2011.

J. E. Hall, Guyton and Hall Textbook of Medical Physiology, 2010.

G. Ciuti, M. Salerno, G. Lucarini, P. Valdastri, A. Arezzo, A. Menciassi, M. Morino, P. Dario, "A Comparative Evaluation of Control Interfaces for a Robotic-Aided Endoscopic Capsule Platform", IEEE Transactions on Robotics, 2012, vol. 28, N. 2, pp. 534-538.

Mayo Clinic Health System, "EGD—Mayo Clinic Health System," 2013. [Online]. Available: http://mayoclinichealthsystem.org/locations/eau-claire/medical-services/gastroenterology-and-hepatology/egd.

M. Moshkowitz, Y. Hirsch, I. Carmel, T. Duvdevany, I. Fabian, E. P. Willenz, and J. Cohen, "A Novel Device for Rapid Cleaning of Poorly Prepared Colons," Endoscopy, vol. 42, pp. 834-836, 2010.

P. Valdastri, M. Simi, and R. J. Webster III, "Advanced Technologies for Gastrointestinal Endoscopy," Annu. Review of Biomed. Eng., vol. 14, pp. 397-429, 2012.

L. Ascari, C. Stefanini, A. Menciassi, S. Sahoo, P. Rabischong, and P. Dario, "A New Active Microendoscope for Exploring the Subarachnoid Space in the Spinal Cord," 2003 IEEE Int. Cont Robot. Autom., vol. 2, pp. 2657-2667, 2003.

A. Ferro, B. Peleteiro, M. Malvezzi, C. Bosetti, P. Bertuccio, F. Levi, E. Negri, C. La Vecchia, and N. Lunet, "Worldwide Trends in Gastric Cancer Mortality (1980-2011), with Predictions to 2015, and Incidence by Subtype," Eur. J. Cancer, vol. 50, No. 7, pp. 1330-1344, May 2014.

PCT International Search Report and Written Opinion for PCT Application No. PCT/US2015/049142 dated Dec. 11, 2015.

Toennies, J.L. et al., "A Wireless Insufflation System for Capsular Endoscopes," Journal of Medical Devices, vol. 3 (Jun. 2009).

Toennies, Jenna L. et al., "Initial Feasibility Studies on Wireless Insufflation of the GI Tract," IEEE International Conference on Robotics and Automation 2010—Workshop on Meso-ScaleRobotics for Medical Interventions, (May 3, 2010).

Smith, Byron, "Wireless Insufflation for Wireless Capsule Endoscopy," Vanderbilt University Master's Thesis (Aug. 2012).

Pedersen, Amanda, "Capsule Endoscopy in ER Could Drop Admission Rate," Medical Device Daily (Feb. 13, 2013).

Lehman, A.C. et al., "Surgery with Cooperative Robots," Comput. Aided. Surg., 13(2), pp. 95-105 (Mar. 2008).

Cadeddu, J.A. et al., "Novel magnetically guided intra-abdominal camera to facilitate laparoendoscopic single site surgery: initial human experience," Surg. Endoscopy, 23, pp. 1984-1899 (May 9, 2009).

C. S. Bell, K. L. Obstein, P. Valdastri, "Image partitioning and illumination in image-based pose detection for teleoperated flexible endoscopes", Artificial Intelligence in Medicine, 2013, in press.

M. Beccani, C. Di Natali, L. Sliker, J. Schoen, M. E. Rentschler, P. Valdastri, "Wireless Tissue Palpation for Intraoperative Detection of Lumps in Soft Tissue", IEEE Transactions on Biomedical Engineering, 2013, in press.

M. Simi, G. Gerboni, A. Menciassi, P. Valdastri, "Magnetic Torsion Spring Mechanism for a Wireless Biopsy Capsule", ASME Journal of Medical Devices, 2013, in press.

A. Arezzo, A. Menciassi, P. Valdastri, G. Ciuti, G. Lucarini, M. Salerno, C. Di Natali, M. Verra, P. Dario, M. Morino, "Experimental assessment of a novel robotically-driven endoscopic capsule compared to traditional colonoscopy", Digestive and Liver Disease, 2013, vol. 45, N. 8, pp. 657-662.

(56) References Cited

OTHER PUBLICATIONS

C. Di Natali, M. Beccani, P. Valdastri, "Real-Time Pose Detection for Magnetic Medical Devices", IEEE Transactions on Magnetics, 2013, vol. 49, N. 7, pp. 3524-3527.
M. Simi, R. Pickens, A. Menciassi, S. D. Herrell, P. Valdastri, "Fine tilt tuning of a laparoscopic camera by local magnetic actuation: Two-Port Nephrectomy Experience on Human Cadavers", Surgical Innovation, 2013, vol. 20, N. 4, pp. 385-394.
J. L. Gorlewicz, S. Battaglia, B. F. Smith, G. Ciuti, J. Gerding, A. Menciassi, K. L. Obstein, P. Valdastri, R. J. Webster III, "Wireless Insufflation of the Gastrointestinal Tract", IEEE Transactions on Biomedical Engineering, 2013, vol. 60, N. 5, pp. 1225-1233.
T. Horeman, D. D. Kurteva, P. Valdastri, F. W. Jansen, J. J. van den Dobbelsteen, J. Dankelman, "The Influence of Instrument Configuration on Tissue Handling Force in Laparoscopy", Surgical Innovation, 2013, vol. 20, N. 3, pp. 260-267.
M. Simi, M. Silvestri, C. Cavallotti, M. Vatteroni, P. Valdastri, A. Menciassi, P. Dario, "Magnetically Activated Stereoscopic Vision System for Laparoendoscopic Single Site Surgery", IEEE/ASME Transactions on Mechatronics, 2013, vol. 18, N. 3, pp. 1140-1151.
K. L. Obstein, S. Battaglia, B. F. Smith, J. S. Gerding, P. Valdastri, "Novel approach for colonic insufflation via an untethered capsule (with video)", Gastrointestinal Endoscopy, 2013, vol. 77, N. 3, pp. 516-517.
K. Obstein, P. Valdastri, "Advanced Endoscopic Technologies for Colorectal Cancer Screening", World Journal of Gastroenterology, 2013, vol. 19, N. 4, pp. 431-439.
P. Valdastri, M. Simi, R. J. Webster III, "Advanced Technologies for Gastrointestinal Endoscopy", Annual Review of Biomedical Engineering, 2012, vol. 14, pp. 397-429.
G. Ciuti, N. Pateromichelakis, M. Sfakiotakis, P. Valdastri, A. Menciassi, D. P. Tsakiris, P. Dario, "A wireless module for vibratory motor control and inertial sensing in capsule endoscopy", Sensors and Actuators A: Physical, 2012, vol. 186, pp. 270-276.
J. Valdastri, G. Ciuti, A. Verbeni, A. Menciassi, P. Dario, A. Arezzo, M. Morino, "Magnetic air capsule robotic system: Proof of concept of a novel approach for painless colonoscopy", Surgical Endoscopy, 2012, vol. 26, N. 5, pp. 1238-1246.
M. Salerno, G. Ciuti, G. Lucarini, R. Rizzo, P. Valdastri, A. Menciassi, A. Landi, P. Dario, "A discrete-time localization method for capsule endoscopy based on on-board magnetic sensing", Measurement Science and Technology, 2012, 23 015701 (10pp).
C. Cavallotti, P. Merlino, M. Vatteroni, P. Valdastri, A. Abramo, A. Menciassi, P. Dario, "An FPGA-based flexible demo-board for endoscopic capsule design optimization", Sensors and Actuators A: Physical, 2011, vol. 172, No. 1, pp. 301-307.
M. Silvestri, M. Simi, C. Cavallotti, M. Vatteroni, V. Ferrari, C. Freschi, P. Valdastri, A. Menciassi, P. Dario, "Autostereoscopic Three-Dimensional Viewer Evaluation Through Comparison With Conventional Interfaces in Laparoscopic Surgery", Surgical Innovation, 2011, vol. 18, No. 3, pp. 223-230.
P. Valdastri, E. Sinibaldi, S. Caccavaro, G. Tortora, a. Menciassi, P. Dario, "A novel magnetic actuation system for miniature swimming robots", IEEE Transactions on Robotics, 2011, vol. 27, No. 4, pp. 769-779.
J. Pensabene, P. Valdastri, S. Tognarelli, A. Menciassi, A. Arezzo, P. Dario, "Mucoadhesive film for anchoring assistive surgical instruments in endoscopic surgery: in vivo assessment of deployment and attachment", Surgical Endoscopy, 2011, vol. 25, No. 9, pp. 3071-3079.
P. Valdastri, E. Susilo, T. Förster, C. Strohhofer, A. Menciassi, P. Dario, "Wireless implantable electronic platform for chronic fluorescent-based biosensors", IEEE Transactions on Biomedical Engineering, 2011, vol. 58, No. 6, pp. 1846-1854.
M. Vatteroni, P. Valdastri, A. Sartori, A. Menciassi, P. Dario, "Linear-logarithmic CMOS pixel with tunable dynamic range", IEEE Transactions on Electron Devices, 2011, vol. 58, No. 4, pp. 1108-1115.
S. Tognarelli, V. Pensabene, S. Condino, P. Valdastri, A. Menciassi, A. Arezzo, P. Dario, "A pilot study on a new anchoring mechanism for surgical applications based on mucoadhesives", Minimally Invasive Therapy & Allied Technologies, 2011, vol. 20, No. 1, pp. 3-13.
M. Piccigallo, U. Scarfogliero, C. Quaglia, G. Petroni, P. Valdastri, A. Menciassi, P. Dario, "Design of a novel bimanual robotic system for single-port laparoscopy", IEEE/ASME Transactions on Mechatronics, 2010, vol. 15, No. 6, pp. 871-878.
M. Vatteroni, D. Covi, C. Cavallotti, P. Valdastri, A. Menciassi, P. Dario, A. Sartori, "Smart optical CMOS sensor for endoluminal applications", Sensors and Actuators A: Physical, 2010, vol. 162, No. 2, pp. 297-303.
D. Covi, C. Cavallotti, M. Vatteroni, L. Clementel, P. Valdastri, A. Menciassi, P. Dario, A. Sartori, "Miniaturized digital camera system for disposable endoscopic applications", Sensors and Actuators A: Physical, 2010, vol. 162, No. 2, pp. 291-296.
E. Buselli, V. Pensabene, P. Castrataro, P. Valdastri, A. Menciassi, P. Dario, "Evaluation of friction enhancement through soft polymer micro-patterns in active capsule endoscopy", Measurement Science and Technologies, 2010, 21 105802 (7pp).
P. Valdastri, C. Quaglia, E. Buselli, A. Arezzo, N. Di Lorenzo, M. Morino, A. Menciassi, P. Dario, "A Magnetic Internal Mechanism for Camera Steering in Wireless Endoluminal Applications", Endoscopy, 2010, vol. 42, pp. 481-486.
J. L. Toennies, G. Tortora, M. Simi, P. Valdastri, R. J. Webster III, "Swallowable Medical Devices for Diagnosis and Surgery: The State of the Art", Proceedings of the Institution of Mechanical Engineers, Part C: Journal of Mechanical Engineering Science, 2010, vol. 224, No. 7, pp. 1397-1414.
M. Simi, G. Ciuti, S. Tognarelli, P. Valdastri, A. Menciassi, P. Dario, "Magnetic link design for a robotic laparoscopic camera", Journal of Applied Physics, 2010, vol. 107, No. 9, pp. 09B302-09B302-3.
M. Simi, P. Valdastri, C. Quaglia, A. Menciassi, P. Dario, "Design, Fabrication and Testing of an Endocapsule with Active Hybrid Locomotion for the Exploration of the Gastrointestinal Tract", IEEE Transactions on Mechatronics, 2010, vol. 15, No. 2, pp. 170-180.
G. Ciuti, R. Donlin, P. Valdastri, A. Arezzo, A. Menciassi, M. Morino, P. Dario, "Robotic versus manual control in magnetic steering of an endoscopic capsule", Endoscopy, 2010, vol. 42, pp. 148-152.
G. Ciuti, P. Valdastri, A. Menciassi, P. Dario, "Robotic magnetic steering and locomotion of capsule endoscope for diagnostic and surgical endoluminal procedures", Robotica, 2010, vol. 28, No. 2, pp. 199-207.
R. Carta, G. Tortora, J. Thoné, B. Lenaerts, P. Valdastri, A. Menciassi, R. Puers, P. Dario, "Wireless powering for a self-propelled and steerable endoscopic capsule for stomach inspection", Biosensors and Bioelectronics, 2009, vol. 25, No. 4, pp. 845-851.
C. Quaglia, E. Buselli, R. J. Webster III, P. Valdastri, A. Menciassi, P. Dario, "An Endoscopic Capsule Robot: A Meso-Scale Engineering Case Study", Journal of Micromechanics and Microengineering, 2009, vol. 19, No. 10, 105007 (11pp).
G. Tortora, P. Valdastri, E. Susilo, A. Menciassi, P. Dario, F. Rieber, M. O. Schurr, "Propeller-based wireless device for active capsular endoscopy in the gastric district", Minimally Invasive Therapy & Allied Technologies, 2009, vol. 18, No. 5, pp. 280-290.
E. Susilo, P. Valdastri, A. Menciassi, P. Dario, "A Miniaturized Wireless Control Platform for Robotic Capsular Endoscopy Using Advanced Pseudokernel Approach", Sensors and Actuators A: Physical, 2009, vol. 156, No. 1, pp. 49-58.
C. Cavallotti, M. Piccigallo, E. Susilo, P. Valdastri, A. Menciassi, P. Dario, "An Integrated Vision System with Autofocus for Wireless Capsular Endoscopy", Sensors and Actuators A: Physical, 2009, vol. 156, No. 1, pp. 72-78.
P. Valdastri, R. J. Webster III, C. Quaglia, M. Quirini, A. Menciassi, P. Dario, "A New Mechanism for Meso-Scale Legged Locomotion in Compliant Tubular Environments", IEEE Transactions on Robotics, 2009, vol. 25, No. 5, pp. 1047-1057.
P. Valdastri, S. Tognarelli, A. Menciassi, P. Dario, "A scalable platform for biomechanical studies of tissue cutting forces", Measurement Science and Technology, 2009, vol. 20, 045801 (11pp).

(56) References Cited

OTHER PUBLICATIONS

E. Buselli, P. Valdastri, M. Quirini, A. Menciassi, P. Dario, "Superelastic leg design optimization for an endoscopic capsule with active locomotion", Smart Materials and Structures, 2009, vol. 18, 015001 (8pp).

P. Valdastri, C. Quaglia, E. Susilo, A. Menciassi, P. Dario, C.N. Ho, G. Anhoeck, M.O. Schurr, "Wireless Therapeutic Endoscopic Capsule: in-vivo Experiment", Endoscopy, 2008, vol. 40, pp. 979-982.

P. Valdastri, A. Menciassi, P. Dario, "Transmission Power Requirements for Novel ZigBee Implants in the Gastrointestinal Tract", IEEE Transactions on Biomedical Engineering, 2008, vol. 55, No. 6, pp. 1705-1710.

P. Valdastri, S. Rossi, A. Menciassi, V. Lionetti, F. Bernini, F. A. Recchia, P. Dario, "An Implantable ZigBee Ready Telemetric Platform for In Vivo Monitoring of Physiological Parameters", Sensors and Actuators A: Physical, 2008, vol. 142, No. 1, pp. 369-378.

A. Sieber, P. Valdastri, K. Houston, C. Eder, O. Tonet, A. Menciassi, P. Dario, "A Novel Haptic Platform for Real Time Bilateral Biomanipulation with a MEMS Sensor for Triaxial Force Feedback", Sensors and Actuators A: Physical, 2008, vol. 142, No. 1, pp. 19-27.

A. Sieber, P. Valdastri, K. Houston, A. Menciassi, P. Dario, "Flip Chip Microassembly of a Silicon Triaxial Force Sensor on Flexible Substrates", Sensors and Actuators A: Physical, 2008, vol. 142, No. 1, pp. 421-428.

L. Beccai, S. Roccella, L. Ascari, P. Valdastri, A. Sieber, M. C. Carrozza, P. Dario, "Development and Experimental Analysis of a Soft Compliant Tactile Microsensor to be Integrated in an Antropomorphic Artificial Hand", IEEE/ASME Transactions on Mechatronics, 2008, vol. 13, No. 2, pp. 158-168.

C. Oddo, P. Valdastri, L. Beccai, S. Roccella, M.C. Carrozza, P. Dario, "Investigation on calibration methods for multi-axis, linear and redundant force sensors", Measurement Science and Technology, 2007, vol. 18, pp. 623-631.

J. Valdastri, K. Houston, A. Menciassi, P. Dario, A. Sieber, M. Yanagihara, M. Fujie, "Miniaturised Culling Tool with Triaxial Force Sensing Capabilities for Minimally Invasive Surgery", ASME Journal of Medical Devices, 2007, vol. 1, N. 3, pp. 206-211.

G. Turchetti, B. Labella, P. Valdastri, A. Menciassi, P. Dario, "The importance of giving an alternative: the case of fetal surgery", Int. J. Healthcare Technology and Management, 2007, vol. 8, Nos. 3-4, pp. 250-267.

P. Valdastri, K. Harada, A. Menciassi, L. Beccai, C. Stefanini, M. Fujie, and P. Dario, "Integration of a Miniaturised Triaxial Force Sensor in a Minimally Invasive Surgical Tool", IEEE Transactions on Biomedical Engineering, 2006, vol. 53, No. 11, 2397-2400.

P. Valdastri, P. Corradi, A. Menciassi, T. Schmickl, K. Crailsheim, J. Seyfried, P. Dario, "Micromanipulation, Communication and Swarm Intelligence Issues in a Swarm Microrobotic Platform", Robotics and Autonomous Systems, 2006, vol. 54, No. 10, pp. 789-804.

P. Valdastri, S. Roccella, L. Beccai, E. Galin, A. Menciassi, M. C. Carrozza, P. Dario, "Characterization of a novel hybrid silicon three-axial force sensor", Sensors and Actuators A: Physical, 2005, vol. 123-124C, pp. 249-257.

L. Beccai, S. Roccella, A. Arena, F. Valvo, P. Valdastri, A. Menciassi, M. C. Carrozza, P. Dario, "Design and fabrication of a hybrid silicon three axial force sensor for biomechanical applications", Sensors and Actuators A: Physical, 2005, vol. 120, No. 2, pp. 370-382.

J. Valdastri, A. Menciassi, A. Arena, C. Caccamo, and P. Dario, "An Implantable Telemetry Platform System for in vivo Monitoring of Physiological Parameters", IEEE Transactions on Information Technology in Biomedicine, 2004, vol. 8, No. 3, pp. 271-278.

X. Wang, C. Di Natali, M. Beccani, M. Kern, P. Valdastri, M. Rentschler, "Novel Medical Wired Palpation Device: A Device Validation Study of Material Properties", Transducers 2013, Barcelona, Spain, pp. 1653-1658.

M. Beccani, C. Di Natali, M. E. Rentschler, P. Valdastri, "Wireless Tissue Palpation: Proof of Concept for a Single Degree of Freedom", IEEE International Conference on Robotics and Automation (ICRA) 2013, Karlsruhe, Germany, pp. 703-709.

M. Beccani, C. Di Natali, M. Rentschler, P. Valdastri, "Uniaxial Wireless Tissue Palpation Device for Minimally Invasive Surgery", ASME Design of Medical Devices Conference, Apr. 2013, Minneapolis, Minnesota, ASME Journal of Medical Devices, vol. 7, N. 2, 020919 (3 pp).

C. Di Natali, P. Valdastri "Remote active magnetic actuation for a single-access surgical robotic manipulator", in Proc. of the XVI Annual Conference of the International Society for Computer Aided Surgery (ISCAS) 2012, Pisa, Italy, Jun. 2012, International Journal of Computer Assisted Radiology and Surgery, 2012, vol. 7, Suppl. 1, pp. S169-S170.

C. Di Natali, T. Ranzani, M. Simi, A. Menciassi, P. Valdastri "Trans-abdominal Active Magnetic Linkage for Robotic Surgery: Concept Definition and Model Assessment", in Proc. of IEEE International Conference on Robotics and Automation (ICRA) 2012, St Paul, MN, USA, May 2012, pp. 695-700.

M. Simi, G. Gerboni, A. Menciassi, P. Valdastri, "Magnetic Mechanism for Wireless Capsule Biopsy", in Proc. of ASME Design of Medical Devices Conference, Apr. 10-12, 2012, Minneapolis, MN, ASME Journal of Medical Devices, vol. 6, p. 017611-1.

T. Ranzani, C. Di Natali, M. Simi, A. Menciassi, P. Dario, P. Valdastri, "A Novel Surgical Robotic Platform Minimizing Access Trauma", in Proc. of 4th Hamlyn Symposium on Medical Robotics, London, UK, Jun. 2011, pp. 15-16.

J. Valdastri, G. Ciuti, A. Verbeni, A. Menciassi, P. Dario, A. Arezzo, M. Morino, "Magnetic air capsule robotic system: a novel approach for painless colonoscopy", 19th International Congress of the European Association of Endoscopic Surgery (EAES) in Turin, Italy.

M. Simi, G. Sardi, P. Valdastri, A. Menciassi, P. Dario, "Magnetic Levitation Camera Robot for Endoscopic Surgery", in Proc. of IEEE International Conference on Robotics and Automation (ICRA) 2011, Shanghai, China, May 2011, pp. 5279-5284.

O. Alonso, J. Canals, L. Freixas, J. Samitier, A. Dieguez, M. Vatteroni, E. Susilo, C. Cavallotti, P. Valdastri, "Enabling multiple robotic functions in an endoscopic capsule for the entire gastrointestinal tract exploration", in Proc. ESSCIRC, 2010, pp. 386-389.

Yamamoto et al., "Techniques for Environment Parameter Estimation During Telemanipulation," pp. 217-223, 2008.

PCT International Search Report and Written Opinion for Application No. PCT/EP2011/064764 dated Oct. 10, 2011.

PCT International Search Report and Written Opinion for Application No. PCT/IB2012/052739 dated Aug. 7, 2012.

PCT International Search Report and Written Opinion for Application No. PCT/US2014/012086 dated May 14, 2014.

European Patent Office Search Report for Application No. 15840650.4 dated May 28, 2018, 8 pages.

McCreery et al., "Feasibility of locating tumours in lung via kinaesthetic feedback." The International Journal of Medical Robotics and Computer Assisted Surgery, vol. 4, No. 1, pp. 58-68, 2008.

Miller et al., "Tactile imaging system for localizing lung nodules during video assisted thoracoscopic surgery," 2007, pp. 2996-3001.

Misra et al., "Environment Parameter Estimation during Bilateral Telemanipulation," in IEEE Virtual Reality Conference (VR'06), 2006, No. 1, pp. 100-100.

Moll et al., "Reconstructing shape from motion using tactile sensors," 2001, vol. 2, pp. 692-700.

Naish et al., "Effect of Velocity Control on Kinesthetic Lung Tumour Localization," in 21st Canadian Conference on Electrical and Computer Engineering, 2008, vol. 1345, pp. 1337-1340.

National Digestive Diseases Information Clearinghouse, https://www.niddk.nih.gov/health-information/digestive-diseases.

Noonan et al., "A dual-function wheeled probe for tissue viscoelastic property identification during minimally invasive surgery," 2007, pp. 2629-2634.

Ohtsuka et al., "Application of a new tactile sensor to thoracoscopic surgery: Experimental and clinical study," The Annals of Thoracic Surgery, vol. 60, No. 3, pp. 610-614, 1995.

Okamura et al., "Feature Guided Exploration with a Robotic Finger," 2001, pp. 589-596.

Okamura et al., "Overview of dexterous manipulation," 2000, vol. 1, pp. 255-262.

(56) References Cited

OTHER PUBLICATIONS

Ottensmeyer et al., "In vivo data acquisition instrument for solid organ mechanical property measurement," in Medical Image Computing and Computer-Assisted Intervention—MICCAI 2001. Springer, 2001, pp. 975-982.
Patterson et al., "The Pig as an Experimental Model for Elucidating the Mechanisms Governing Dietary Influence on Mineral Absorption," Experimental biology and medicine, 2008; 233(6):651-64.
Pilz et al., "Colon capsule endoscopy compared to conventional colonoscopy under routine screening conditions," BMC Gastroenterology, 2010; 10:66.
Puangmali et al., "Miniature 3-axis distal force sensor for minimally invasive surgical palpation," IEEE/ASME Trans. Mechatronics, vol. 17, No. 4, pp. 646-656, 2012.
Puangmali et al., "Optical Fiber Sensor for Soft Tissue Investigation during Minimally Invasive Surgery," in 2008 IEEE International Conference on Robotics and Automation, 2008, pp. 2934-2938.
Quirini et al., Feasibility proof of a legged locomotion capsule for the GI tract. Gastrointestinal Endoscopy, 67:1153-1158, 2008.
Randolph et al., "Recurrent laryngeal nerve identification and assessment during thyroid surgery: laryngeal palpation," World journal of surgery, vol. 28, No. 8, pp. 755-760, Aug. 2004.
Rosen et al., "Biomechanical properties of abdominal organs in vivo and postmortem under compression loads," Journal of Biomechanical Engineering, vol. 130, No. 021020, pp. 1-17, 2008.
Rucker et al., "A Geometrically Exact Model for Externally Loaded Concentric-Tube Continuum Robots.," IEEE transactions on robotics : a publication of the IEEE Robotics and Automation Society, vol. 26, No. 5, pp. 769-780, Jan. 2010.
Rucker et al., "Computing Jacobians and compliance matrices for externally loaded continuum robots," in 2011 IEEE International Conference on Robotics and Automation, 2011, No. 3, pp. 945-950.
Rucker et al., "Equilibrium Conformations of Concentric-tube Continuum Robots," The International Journal of Robotics Research, vol. 29, No. 10, pp. 1263-1280, Apr. 2010.
Sabatini et al., "Interpretation of mechanical properties of soft tissues from tactile measurements," vol. 139, 1990, pp. 152-162.
Samur et al., "A robotic indenter for minimally invasive measurement and characterization of soft tissue response," Medical Image Analysis, vol. 11, No. 4, pp. 361-373, 2007.
Sangpradit et al., "Tissue identification using inverse finite element analysis of rolling indentation," 2009, pp. 1250-1255.
Sauk et al., "Optical enhancements in diagnosis and surveillance of colorectal neoplasia," Curr Colorectal Cancer Rep, 2011; 7: 24-32.
Scheidler et al., Virtual colonoscopy using ct and mri. Radiologe, 38(10):824-31, 1998.
Schindler et al., "Foaming at the mouth: Ingestion of Hydrogen Peroxide Solution (with video)," Clinical jastroenterology and hepatology, Feb. 2012; 10(2): e13-4.
Segnan et al., Comparing attendance and detection rate of colonoscopy with sigmoidoscopy and FIT for colorectal cancer screening. Gastroenterology, 132(7):2304-2312, Jun. 2007.
Seidell, Solubilities of inorganic and organic substances. New York, D. Van Nostrand company, 2nd edition, 1907.
Simaan et al., "Design and Integration of a Telerobotic System for Minimally Invasive Surgery of the Throat," International Journal of Robotics Research—special issue on Medical Robotics (special Issue on Medical Robotics), vol. 28, No. 9, pp. 1134-1153, 2009.
Simaan, "Snake-Like Units Using Flexible Backbones and Actuation Redundancy for Enhanced Miniaturization," in IEEE International Conference on Robotics and Automation, 2005, pp. 3020-3028.
Song et al., "Mechanical properties of the human abdominal wall measured in vivo during insufflation for laparoscopic surgery," Surgical Endoscopy, vol. 20, No. 6, pp. 987-990, 2006.
Sonnenberg et al., "Is virtual colonoscopy a cost-effective option to screen for colorectal cancer?" Am J Gastroenterol. Aug. 1999;94(8):2268-74.
Sosna et al., "Colonic perforation at CT colonography:assessment of risk in a multicenter large cohort," Radiology. 2006; 239(2):457-63.
Stark et al., "The future of telesurgery: a universal system with haptic sensation," Journal of the Turkish-German Gynecological Association, vol. 13, No. 1, pp. 74-76, 2012.
Stevenson, "Pain following colonoscopy: elimination with carbon dioxide," Gastrointestinal Endoscopy, pp. 564-567, 1992.
Takktile by Y. Tenzer, L. Jentoft, I. Daniher, and Robert Howe: www.takktile.com.
The Center for Disease Control and Prevention, "Colorectal cancer screening basic fact sheet," 2017, 2 pages.
Tholey et al., "A compact and modular laparoscopic grasper with tri-directional force measurement capability," ASME Journal of Medical Devices, vol. 2, No. 3, pp. 031 001-031 009, 2008.
Tully et al., "Constrained Filtering with Contact Detection Data for the Localization and Registration of Continuum Robots in Flexible Environments," Proceedings—IEEE International Conference on Robotics and Automation, 2012, 3388-3394.
Van Der Meijden et al., "The value of haptic feedback in conventional and robot-assisted minimal invasive surgery and virtual reality training: a current review," Surgical Endoscopy, vol. 23, pp. 1180-1190, 2009.
Webster et al., "Design and Kinematic Modeling of Constant Curvature Continuum Robots: A Review," The International Journal of Robotics Research, vol. 29, No. 13, pp. 1661-1683, Jun. 2010.
Webster et al., "Mechanics of Precurved-Tube Continuum Robots," IEEE Transactions on Robotics, vol. 25, No. 1, pp. 67-78, Feb. 2009.
Wellman et al., "Extracting Features from Tactile Maps," Proceedings of the Second International Conference on Medical Image Computing and Computer-Assisted Intervention, vol. 167, pp. 11-1142, 1999.
Wellman et al., "Tactile Imaging of Breast Masses: First Clinical Report," vol. 136, No. 2, pp. 204-248, 2001.
Wellman et al., "Tactile imaging: a method for documenting breast lumps," 1999, vol. 2, p. 1131.
White et al., "Surgical Technique: Static Intramedullary Nailing of the Femur and Tibia Without Intraoperative Fluoroscopy.," Clinical orthopaedics and related research, pp. 3469-3476, Mar. 2011.
Wilkins et al., The current state of flexible sigmoidoscopy training in family medicine residency programs. Family Medicine, 37:706-11, 2005.
Wilkins et al., "Colorectal cancer: A summary of the evidence for screening and prevention," Am Fam Physician. Dec. 15, 2008;78(12):1385-1392.
Xu et al., "Actuation Compensation for Flexible Surgical Snake-like Robots with Redundant Remote Actuation," in IEEE International Conference on Robotics and Automation, 2006, pp. 4148-4154.
J. L. Toennies, G. Ciuti, B. F. Smith, A. Menciassi, P. Valdastri, and Robert J. Webster III, "Toward Tetherless Insufflation of the GI Tract", in Proc. IEEE Engineering in Medicine and Biology Society Conference (EMBC) 2010, Buenos Aires, Argentina, Sep. 2010, pp. 1946-1949.
G. Tortora, S. Caccavaro, P. Valdastri, A. Menciassi, P. Dario, "Design of an autonomous jellyfish miniature robot Based on a novel concept of magnetic actuation", in Proc. of IEEE International Conference on Robotics and Automation (ICRA) 2010, Anchorage, AK, USA, May 2010, pp. 1592-1597.
L. S. Chiang, P. S. Jay, P. Valdastri, A. Menciassi, P. Dario, "Tendon Sheath Analysis for Prediction of Distal End Force and Elongation", in Proc. IEEE/ASME Conference on Advanced Intelligent Mechatronics 2009, Singapore, Jul. 2009, pp. 332-337.
O. Tonet, M. Marinelli, G. Megali, A. Sieber, P. Valdastri, A. Menciassi, P. Dario, "Control of a teleoperated nanomanipulator with time delay under direct vision feedback", In Proc. of IEEE International Conference on Robotics and Automation (ICRA) 2007, Rome, Italy, Apr. 2007, pp. 3514-3519.
J. L. Toennies, R. J. Webster III, P. Valdastri, "Mesoscale Mobile Robots for Gastrointestinal Minimally Invasive Surgery (MIS)", Chapter 10, pp. 224-251, in "Medical Robotics—Minimally Invasive Surgery" edited by Paula Gomes, Woodhead Publishing Series in Biomaterials: No. 51, ISBN 0-85709-130-1 (Aug. 2012).

(56) References Cited

OTHER PUBLICATIONS

A. Menciassi, P. Valdastri, K. Harada, P. Dario, "Single and Multiple Robotic Capsules for Endoluminal Diagnosis and Surgery", Chapter 14, pp. 313-354, in "Surgical Robotics—System Applications and Visions", edited by J. Rosen, B. Hannaford, R. Satava, published by Springer, 1st Edition, 2011, XXII, 819 p. 365 illus, Hardcover, ISBN: 378-1-4419-1125-4.

B. Laulicht, N. Gidmark, A. Tripathl, E. Mathiowitz, "Localization of magnetic pills," Proc. of the National Academy of Sciences, vol. 108, No. 6, 2252-2257 (Feb. 8, 2011).

S. Best, E. Olweny, S. Park, P. Smith, R. Fernandez, D. Scott, R. Bergs, and J. Cadeddu. New generation magnetic camera facilitates porcine LESS nephrectomy. The Journal of Urology, 185:e413-e413, 2011.

"F. Carpi, N. Kastelein, M.Talcott, and C.Pappone. Magnetically controllable gastrointestinal steering ofvideo capsules. IEEE Transactions on Biomedical Engineering, 58:231-234, 2011."

"J. Keller, C. Fibbe, F. Volke, J. Gerber, A. C. Mosse, M. Reimann-Zawadzki, E. Rabinovitz, P. Layer,D. S. and V. Andresen, U. Rosien, and P. Swain. Inspection of the human stomach using remote controlled capsule endoscopy: a feasibility study in healthy volunteers. Gastrointestinal Endoscopy,73:22-28, 2011."

"S. Park, R. Bergs, R. Eberhart, L. Baker, R. Fernandez, and J. Cadeddu. Trocar-less instrumentation forlaparoscopy: magnetic positioning of intra-abdominal camera and retractor Annals of Surgery,245:379-384, 2007."

"J. F. Rey, H. Ogata, N. Hosoe, K. Ohtsuka, N. Ogata, K. Ikeda, H. Aihara, I. Pangtay, T. Hibi, S. Kudo,and H. Tajiri. Feasibility of stomach exploration with a guided capsule endoscope. Endoscopy, 42:541-545, 2010."

"P. Swain, R. Austin, K. Bally, and R. Trusty. Development and testing of a tethered, independentcamera for NOTES and single-site laparoscopic procedures. Surgical Endoscopy, 24:2013-2021, 2010."

"P. Valdastri, G. Ciuti, A. Verbeni, A. Menciassi, P. Dario, A. Arezzo, M. Morino. Magnetic air capsulerobotic system: Proof of concept of a novel approach for painless colonoscopy. Surgical Endoscopy,2011, in press."

"G. Ostrovsky, Preview of Magnetically Guided Colonoscopy from Vanderbilt. MedGadget press release:http://medgadget.com/2011/10/preview-of-magnetically-guided-colonoscopy-from-vanderbilt.html."

"A. Fritscher-Ravens, S. Fox, C.P. Swain, P. Mills, and G. Long. Cathcam guide wire-directedcolonoscopy: first pilot study in patients with a previous incomplete colonoscopy. Endoscopy, 38:209-213, 2006."

"B. Vucelic, D. Rex, R. Pulanic, J. Pfefer, I. Hrstic, B. Levin, Z. Halpern, and N. Arber. The Aer-o-Scope: proof of concept of a pneumatic, skill-independent, self-propelling, self-navigating colonoscope.Gastroenterology, 130:672-677, 2006."

"F. Cosentino, E. Tumino, G.R. Passoni, E. Morandi, and A. Capria. Functional evaluation of theEndotics System, a new disposable self-propelled robotic colonoscope: in vitro tests and clinical trial. International Journal of Artificial Organs, 32:517-527, 2009."

"M. Shike, Z. Fireman, R. Eliakim, O. Segol, A. Sloyer, L.B. Cohen, S. Goldfarb-Albak, and A. Repici.Sightline Colonosight system for a disposable, power-assisted, non-fiber-optic colonoscopy. Gastrointestinal Endoscopy, 68:701-710, 2008."

"T. Rösch, A. Adler, H. Pohl, E. Wettschureck, M. Koch, B. Wiedenmann, and N. Hoepner. A motor-driven single-use colonoscope controlled with a hand-held device: a feasibility study involunteers. Gastrointestinal Endoscopy, 67:1139-1146, 2008"

"A. Eickhoff, J. Van Dam, R. Jakobs, V. Kudis, D. Hartmann, U. Damian, U. Weickert, D. Schilling, andJ.F. Riemann. Computer-assisted colonoscopy (the NeoGuide endoscopy system): results of the firsthuman clinical trial (pace study). The American Journal of Gastroenterology, 102:261-266, 2007."

"M. Moshkowitz, Y. Hirsch, I. Carmel, T. Duvdevany, I. Fabian, E.P. Willenz, and J. Cohen. A noveldevice for rapid cleaning of poorly prepared colons. Endoscopy, 42:834-836, 2010."

"A. Fritscher-Ravens, C. Mosse, T. Mills, K. Ikeda, P. Swain, Colon cleaning during colonoscopy: a newmechanical cleaning device tested in a porcine model. Gastrointestinal Endoscopy, 63:141-143, 2006."

H. Richert, B. Hilgenfeld, and P. Gornert, "Magnetic sensor techniques for new intelligent endoscopic capsules," http://www.vector-project.com/press/article/VECTOR%20article_Richert_MagneticSensorTechniques.pdf, publicly available prior to Sep. 17, 2012.

Than, T. D.; Alici, G.; Zhou, H.; Li, W.; "A Review of Localization Systems for Robotic Endoscopic Capsules," Biomedical Engineering, IEEE Transactions on , vol. 59, No. 9, pp. 2387-2399, Sep. 2012.

NDI Medical's Aurora product, http://www.ndigital.com/medical/products/aurora/, publicly available prior to Sep. 17, 2012.

"M. B. H. Gerald Rogers. The safety of carbon dioxide insufflation during colonoscopic electro-surgical polypectomy. Gastrointestinal Endoscopy, 20:115-117, 1974."

Bracco. Co2 efficient endoscopic insufflator.

"P. E. J.-M. D. Filip Janssens, Jacques Deviere. Carbon dioxide for gut distension duringdigestive endoscopy: Technique and practice survey. World Journal of Gastroenterology, 15(12):1475-1479, 2009."

"F. A. Macrae, K. G. Tan, and C. B. Williams. Towards safer colonoscopy: a report on thecomplications of 5000 diagnostic or therapeutic colonoscopies. Gut, 24(5):376{383, 1983."

"W. J. R. P. Phaosawasdi K, Cooley W. Carbon dioxide-insufflated colonoscopy: an ignoredsuperior technique. Gastrointestinal Endoscopy, 32:330-333, 1986."

"K. Sumanac, I. Zealley, B. M. Fox, J. Rawlinson, B. Salena, J. K. Marshall, G. W. Stevenson,and R. H. Hunt. Minimizing postcolonoscopy abdominal pain by using fCO2g insufflation: Aprospective, randomized, double blind, controlled trial evaluating a new commercially availablefCO2g delivery system. Gastrointestinal Endoscopy, 56(2):190-194, 2002."

"J. C. H. Wong, K. K. Yau, H. Y. S. Cheung, D. C. T. Wong, C. C. Chung, and M. K. W. Li.Towards painless colonoscopy: A randomized controlled trial on carbon dioxide-insufflatingcolonoscopy. ANZ Journal of Surgery, 78(10):871-874, 2008."

* cited by examiner

HYDRO-JET ENDOSCOPIC CAPSULE AND METHODS FOR GASTRIC CANCER SCREENING IN LOW RESOURCE SETTINGS

RELATED APPLICATIONS

This application claims the benefit of U.S. Provisional Application No. 62/048,105, filed Sep. 9, 2015, the entire contents of which are incorporated herein by reference.

BACKGROUND

Gastric cancer is the second leading cause of cancer death worldwide. Screening programs have had a significant impact on mortality in settings such as Japan. Nearly 70% of cases occur in low/middle income countries (LMICs), where endoscopy resources are traditionally limited. The present invention relates to endoscopic systems and methods and, more specifically, to endoscopic screening mechanisms.

SUMMARY

Esophagogastroduodenoscopy (EGD) is a procedure used in the detection of esophageal and stomach cancers. Currently flexible endoscopes are used in EGD to view the esophagus and stomach; however, flexible endoscopes are both expensive and require large additional machinery to disinfect the system once used.

In many parts of the developing world, instances of stomach cancer are steadily rising and access to flexible endoscopes by the general population is minimal due the aforementioned costs and inability to reliably disinfect systems. The Hydro-Jet Endoscopic Capsule (HEC) described herein has a low fabrication cost and can be disposed of after each use, it overcomes the challenges created by flexible endoscope systems. This creates an affordable alternative for endoscopy in large markets such as East Asia, Central America, South America and Eastern Europe.

Currently there are no low cost alternatives to standard endoscopies. This limits the availability of the procedure in the developing world such as East Asia, Central America, South America and Eastern Europe, where esophageal and stomach cancers are rising within the population. The HEC is a novel medical device, firstly, in the fact that it uses an accessible, biocompatible renewable resource (water) for control and maneuverability. Second, the HEC's low manufacturing cost and disposable design allow it to be used without the additional acquisition of expensive sterilization equipment. Lastly, the HEC system's low initial costs allow it to be an affordable system in developing healthcare markets.

In some embodiments, the invention allows for Esophagogastroduodenoscopy (EGD) procedures to be accomplished at low costs and without sterilization/cleaning/processing equipment using a Hydro-Jet Endoscopic Capsule (HEC). This novel approach bypasses the typical expenses of traditional endoscopes which are both expensive to purchase and require additional machinery to clean for reuse.

The HEC is maneuvered within the body using streams of water that are ejected out of the main body of the capsule at particular angles and at particular pressures. A multi-channel soft tether provides high-pressurized water from a water distribution system to a set of intake nozzles on the capsule. Operated by the user using a computer user interface, the water distribution system controls the flow rate of water into each exit channel on the capsule. The HEC's core is capable of carrying a Video Processing Unit (VPU) that relays real-time images during the procedure for both control and diagnosis. The VPU is reusable between procedures without sterilization/cleaning to reduce the overall procedure cost. The HEC itself is also reconfigurable to host existing on-the-market endoscopic cameras and can be setup to use a disposable camera if need arises.

Once an EGD procedure is complete, the VPU is removed from the HEC. The HEC and its multi-channel soft tether are disposed. The VPU is then inserted into a new HEC with multi-channel soft tether for use in the next patient. Various constructions of the systems and methods described herein provide a novel, ultra low-cost (<1-2 USD per case), disposable system for gastric cancer screening for use in resource-limited settings, including rural villages.

In one embodiment, the system includes a 10×26 mm capsule (fabricated from a biocompatible plastic material) with an attached multi-channel soft tether (diameter 5 mm) that provides high-pressure water to four articulated water-jet nozzles in the capsule. A miniature camera with LEDs is placed at the front of the capsule, with cable located in a fifth tether channel. The tether is connected to a water distribution system, which is used to control the flow of water through each channel in the capsule, thus propelling the capsule. The capsule is controlled by an external joystick. The video processing unit presents the camera view on a dedicated monitor. The capsule and soft tether are designed to be disposable and ultra-low cost (unit price <1-2 USD). The endoscopic camera is the only reusable component, fitted with an efficient engagement/disengagement mechanism. Once inside the capsule, the camera is sealed from the external environment and without need for reprocessing after use.

The system was tested for its ability to allow for visualization of key gastric landmarks in a freshly excised stomach from a 40 Kg Yorkshire swine. The landmarks (pylorus, antrum, greater and lesser curvatures, fundus, and cardia) were labeled using a series of laser lights placed external to the stomach and were visible from within the stomach. Six trials were performed by a single endoscopist. Time and identification of the laser labeled landmarks were recorded.

All landmarks were adequately visualized using the system in all trials. The total time for each trial was 6 min 15 sec±1 min 51 sec. All locations were appropriately identified by the endoscopist. A total of 1.35 L±0.4 L of water was utilized for each trial. There was no evidence of gastric perforation or trauma to the porcine model after each trial. The system allowed for visualization of landmarks in a porcine stomach in a safe and efficient manner. This ultra low-cost endoscopy would allow for gastric cancer screening in low resource settings where there is a high incidence of gastric cancer. In vivo porcine survival studies are ongoing.

In another embodiment, the invention provides a medical capsule system including a capsule housing, a multichannel tether, and a plurality of liquid exhaust ports positioned around an outer circumferences of the capsule housing. The capsule housing is configured to be inserted into an anatomical structure of a patient. The multichannel tether is coupled to a rear of the capsule and includes at least one liquid exhaust channel conveying liquid to the capsule housing. The plurality of liquid exhaust ports are each configured to controllably expel liquid at varying rates to affect lateral movement of the capsule housing.

In yet another embodiment, the invention provides a method of performing esophagogastroduodenoscopy using a hydrojet medical capsule system. The medical capsule system includes a capsule housing, a multichannel tether coupled to the rear of the capsule housing, and a plurality of liquid exhaust ports positioned around an outer circumference of the capsule housing to controllably expel liquid at varying rates. The capsule housing is inserted into the patient's esophagus through the mouth and linearly advanced to the stomach of the patient. Water is provided to the capsule through at least one liquid exhaust channel positioned within the multichannel tether and controllably expelled through one of the plurality of exhaust ports to affect lateral movement of the capsule.

Some embodiments of the invention also provide for detection of tissue damage, esophageal and stomach cancer, and other abnormalities in esophageal and stomach organs.

Other aspects of the invention will become apparent by consideration of the detailed description and accompanying drawings.

DETAILED DESCRIPTION

Before any embodiments of the invention are explained in detail, it is to be understood that the invention is not limited in its application to the details of construction and the arrangement of components set forth in the following description or illustrated in the following drawings. The invention is capable of other embodiments and of being practiced or of being carried out in various ways.

Figure 1:
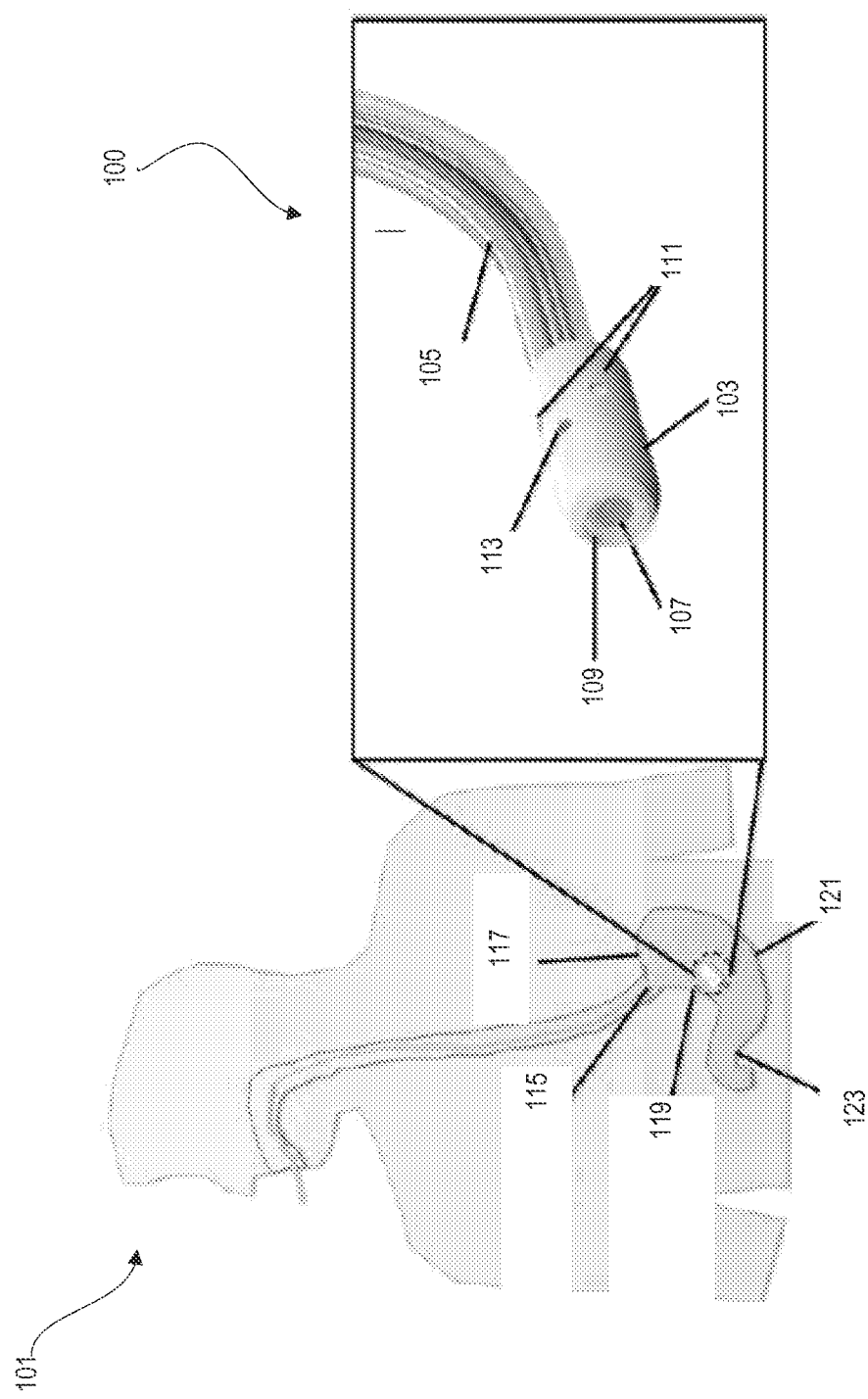
FIG. 1 is a schematic view of a hydrojet capsule according to one embodiment inserted through the mouth of a patient and maneuvered into the stomach.

FIG. 1 illustrates an example of a system and method for performing esophagogastroduodenoscopy (EGD) using a hydrojet endoscopic capsule (HEC) 100. The HEC 100 is maneuvered within the body of a patient 101 using fluidic jets that expel a fluid (typically potable water) out of the main body 103 of the capsule 100. A multi-channel soft tether 105 provides pressurized fluid from a fluid distribution system (described in further detail below) to a set of nozzles on the capsule in order to control the thrust produced by the nozzles. In the example of FIG. 1, the capsule 100 is equipped with a camera 107 and one or more LEDs 109 for illuminating and capturing images of the interior anatomy of the patient 101.

The main body 103 of the capsule 100 includes a plurality of exhaust ports 111 through which the pressurized fluid medium is expelled to control the full hemispherical movement of the capsule within a workspace. One or more suction ports 113 are also positioned on the main body 103 of the capsule 100 and are used to extract fluid from the patient's internal anatomy (e.g., the patient's stomach and/or GI tract) in order to prevent over inflation of the anatomy by the fluid that is injected for maneuvering the capsule 100.

In some embodiments, the capsule 100 is equipped with other sensors including, for example, an inertial sensor. The inertial sensor (e.g., an accelerometer) supplements manual control signals provided by a user and is used to implement closed loop control of the capsule system as described in further detail below.

In the example of FIG. 1, the capsule 100 is inserted through the mouth of the patient 101 and extended through the cardia 115 into the stomach. In the stomach, the jets of the capsule 100 controllably expel fluid through the exhaust ports 111 to maneuver the capsule along the fundus 117, the lesser curvature 119, and the greater curvature 121 towards the pylorus 123.

Figure 2A:
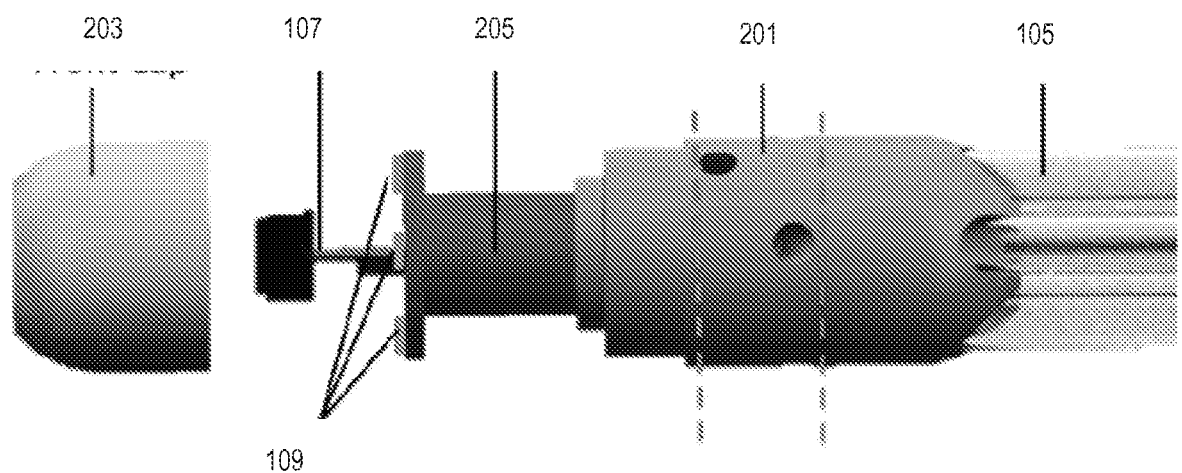
FIG. 2A is an exploded view of the hydrojet capsule of FIG. 1.

FIG. 2A illustrates the capsule 100 in further detail. In the example of FIG. 2A, the main body 103 of the capsule 100 is selectively openable to provide access to a sealed compartment inside the capsule 100. In this example, the main body 103 is opened by detaching an outer shell front cap 203 from the outer shell main body 201. An inner core 205 is positioned inside the main body 103 to provide structural support and to aid in placement of internal components of the capsule 100. The camera 107 extends linearly from the distal end of the inner core 205 and the LEDs 109 are mounted on the distal end of the inner core 205.

Figure 2B:
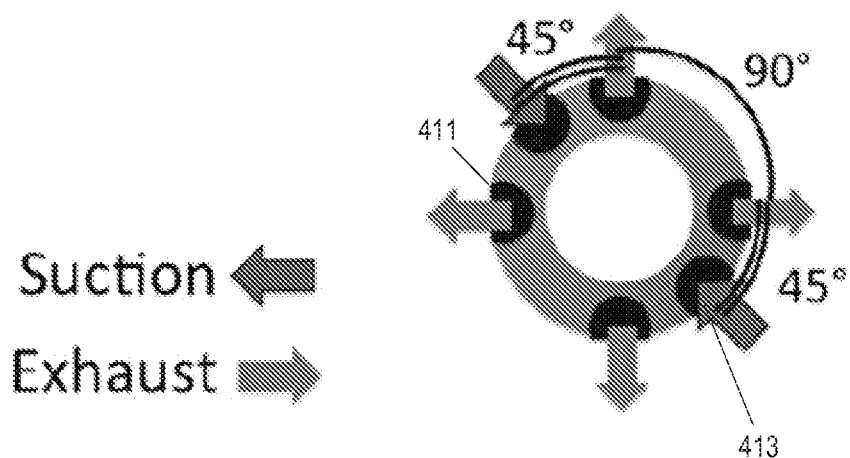
FIG. 2B is a partial cross-sectional view of the main outer shell body of the hydrojet capsule of FIG. 2A.

The exhaust ports 111 and suction ports 113 of the capsule 100 are formed in the outer shell main body 201 of the capsule 100 in this example. As shown in FIG. 2B, four exhaust ports 111 are positioned around the circumference of the main body 103 at 90 degree angles relative to each other. However, it is noted that other quantities and spacings of exhaust ports are possible—for example, a total of three exhaust ports may be positioned around the circumference of the main body at 120 degree angles relative to each other.

Returning to the example of FIGS. 2A and 2B, a pair of suction ports 113 is positioned on opposite sides of the main body 103 at a 45 degree angle relative to the respective neighboring exhaust ports 111. In this example, the exhaust ports 111 are positioned to provide for lateral maneuverability of the capsule 100. For example, to move the capsule 100 to the right, water is controllably expelled from the exhaust port 111 on the left of the capsule main body 103. To dampen the movement of the capsule 100, water may simultaneously be expelled from the exhaust port 111 on the right side of the capsule main body 103 at a lesser flow rate to counteract the thrust produced by the left-side jet. Similarly, to move the capsule 100 laterally upward, water is controllably expelled at a greater flow rate from the exhaust port 111 on the bottom of the capsule main body 103. Furthermore, in some construction, the suction ports are also controllably operated to aid in the lateral movement of the capsule 100 by drawing water to pull the capsule in a particular direction.

Figure 3:
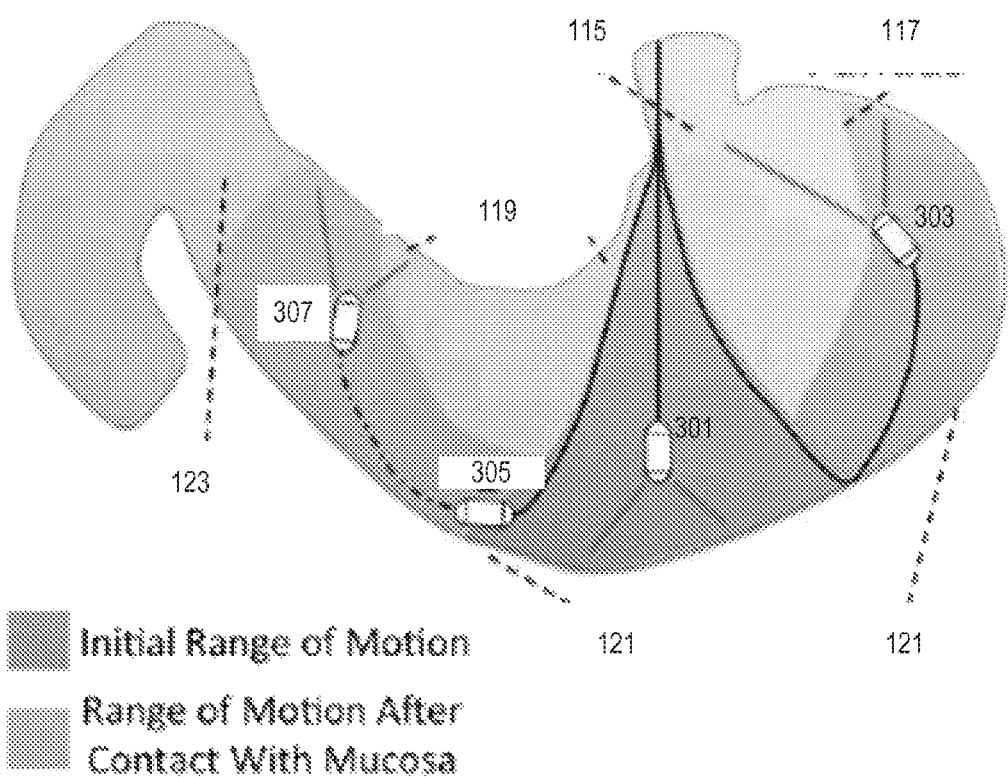
FIG. 3 is another schematic view of the hydrojet capsule of FIG. 1 being maneuvered through the stomach of a patient.

For example, referring to FIG. 3, once the capsule 100 is inserted through the cardia 115 of the stomach (at position 301), the capsule may be turned towards the fundus 117 by expelled fluid through the left-side exhaust port (relative to the reader in FIG. 3). This left-side expulsion will cause the capsule 100 to move along the greater curvature 121 of the stomach towards the fundus 117 (position 303). Conversely, controllably expelling water at a greater pressure through the right-side exhaust port causes the capsule 100 to move to the left (position 305). Continued right-side expulsion combined with continued linear insertion of the capsule 100 causes the capsule 100 to move along the greater curvature 121, crossing the pylorus 123 until it reaches a target position along the lesser curvature 119 (position 307).

As shown in FIG. 3, the capsule 100 has an initial range of motion that can be provided by expelling fluid within the contents of the stomach. However, the range of motion can be extended by contacting the mucosa (e.g., at position 305) and then expelling fluid against the mucosa to generate thrust of the capsule 100.

In some embodiments, linear movement of the capsule 100 is achieved by pushing the flexible tether 105 further into the esophagus of the patient to advance the linear position of the capsule and by pulling the flexible tether to retract the position of the capsule 100. However, in other embodiments, the jets used to expel fluid through the exhaust ports 111 of the capsule 100 are angled towards the rear of the capsule to provide forward and lateral thrust. Similarly, the suction ports 113 can be angles towards the front of the capsule 100 to assist in forward movement of the capsule by drawing water from in front of the capsule 100 to pull the capsule 100 forward.

Furthermore, in addition to controllably expelling fluid through the exhaust ports to cause the capsule to move laterally, the rate at which fluid is expelled can be controlled to stabilize the capsule in a current position.

Figure 4:
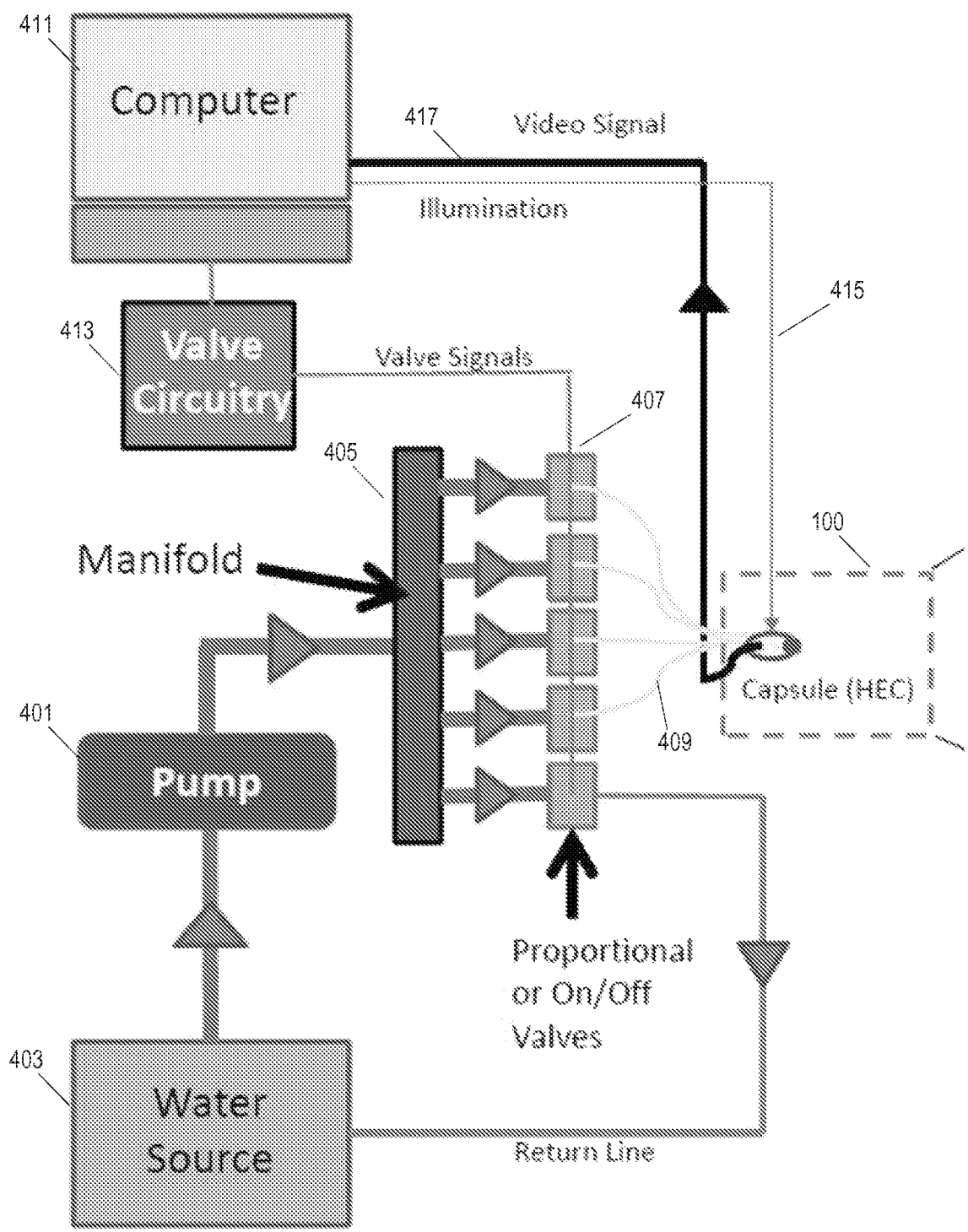
FIG. 4 is a block diagram of a control system for the hydrojet capsule of FIG. 1.

FIG. 4 illustrates an example of a control system for operating and maneuvering the capsule 100. A pump 401 draws fluid from a water source 403 (e.g., a fluid supply tank/reservoir) and provides pressuring water to a fluid manifold 405. A series of controllable valves 407 (either proportional or on/off valves) direct the flow of the pressurized fluid through a series of fluid supply lines 409 to the capsule 100. Each valve 407 and corresponding supply line 409 provides fluid that is expelled through one or more specific exhaust ports 111 on the capsule body. Therefore, the lateral movement of the capsule 100 is controlled by operating the valves 407.

A computer 411 is used to control lateral movement of the capsule by generating output signals to valve controller circuitry 413, which controls the operation of the individual valves 407. The computer 411 may control the valves in response to signals from on-board sensors of the capsule (such as, for example, the accelerometer discussed above). The computer 411 may also interface with one or more user controls (not pictured) through which an operator can guide the movement of the capsule 100. These user controls may include, for example, one or more foot pedals, a joy stick, or other user interface control device. The computer also provides control signals 415 directly to the capsule 100 for operating on-capsule devices such as, for example, the LEDs and the video camera system and also receives data signals 417 from the capsule (e.g., video data from the camera). In some embodiments, the camera data received from the capsule through line 417 is displayed to the user on the computer 411 to aid in the maneuvering and navigation of the capsule 100. The electronic lines 415 and 417 and the fluid supply lines 409 are grouped together and housing within the multi-channel flexible tether of the capsule 100.

Figure 5:
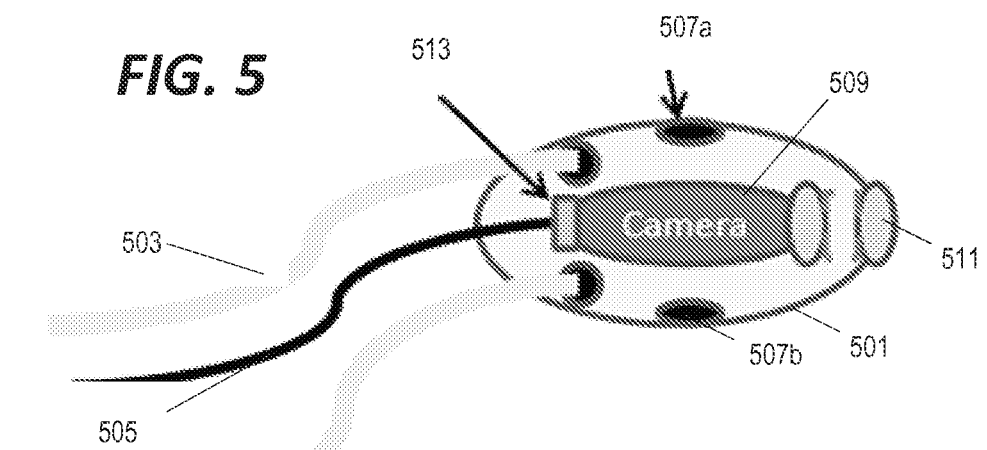
FIG. 5 is a schematic diagram of a hydrojet capsule with a modular tool system.
Figure 6:
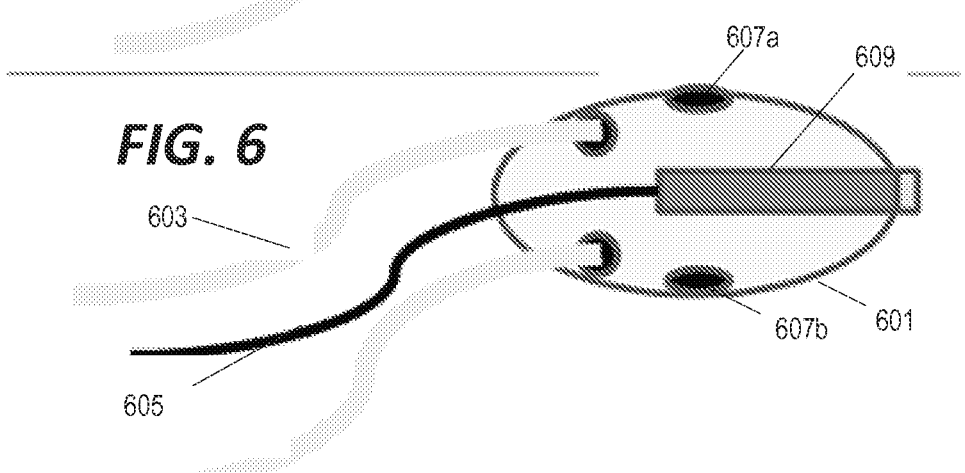
FIG. 6 is a schematic diagram of a hydrojet capsule with a permanently affixed camera system.
Figure 7:
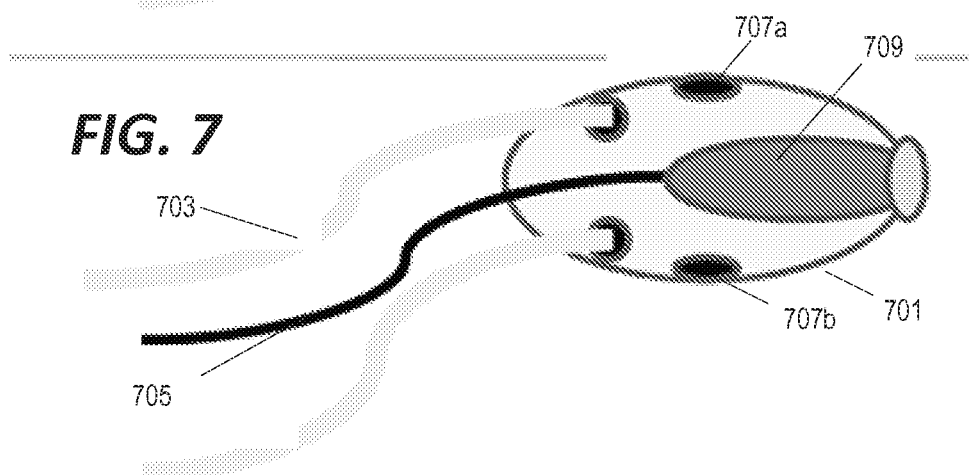
FIG. 7 is a schematic diagram of a disposable hydrojet capsule with a permanently affixed camera system.

FIGS. 5, 6, and 7 further illustrate various examples of the hydrojet capsule 100. The example of FIG. 5 provides a modular capsule that can be selectively fitted with a variety of different tools. Alternatively (or in addition), the capsule system of FIG. 5 can provide a low-cost disposable housing with reusable, more expensive components that are selectively connected to the capsule system and sealed within an internal compartment of the capsule. The example of FIG. 5 includes a selectively operable capsule body 501 with an attached multi-channel tether that provides a plurality of water intake lines 503 and one or more electronic data/power lines 505. Exhaust ports 507a and 507b are positioned around the capsule body. A modular tool 509 is placed within the sealed main body 501 of the capsule. In this example, the modular tool 509 is a video camera system and, as such, the main body 501 is equipped with a lens 511 to enable the video camera system to capture images. The capsule body 501 also includes an electrical connector coupling 513 to connect the modular tool 509 to the electrical data/power line 505.

In reusable modular systems, the camera 509 can be removed and replaced with a different tool/system. However, in disposable systems, the capsule body 501 and the flexible tether are constructed of low-cost materials and are disposed after use. As such, sanitization of the capsule body 501 is not necessary. Furthermore, because the more expensive video camera system 509 is sealed within a compartment of the capsule body 501, the camera system 509 can be reused by coupling the camera system 509 into another capsule body 501 without requiring additional sanitization of the camera system 509.

In the example of FIG. 6, provides another implementation with reusable component that must be sanitized between each use. The main body 601 is coupled to a plurality of fluid supply lines 603 and one or more electrical data/power lines 605. The main body also includes a plurality of exhaust ports 607a, 607b positioned around the capsule body 601 for maneuvering the capsule. However, in this example, the capsule body 601 includes a permanently affixed video camera system 609. Because the video camera system 609 is permanently affixed, the capsule body 601 and the video camera system 609 must be properly sanitized before being reused.

FIG. 7 provides a further example in which a low-cost, permanently affixed camera is included in the capsule system. By using a low-cost camera, the resolution and image quality is reduced. However, the camera system and the capsule can be disposed after use; thereby negating the need for sanitization procedures which can be difficult in some environments/locations. The capsule system of FIG. 7 also includes a disposable main body 701 coupled to a flexible tether that provides a plurality of fluid supply lines 703 and one or more electrical data/power lines 705. The capsule body 701 includes a plurality of exhaust ports 707a, 707b for controlling lateral movement of the capsule and the permanently affixed, low-cost, disposable camera system 709.

Figure 8:
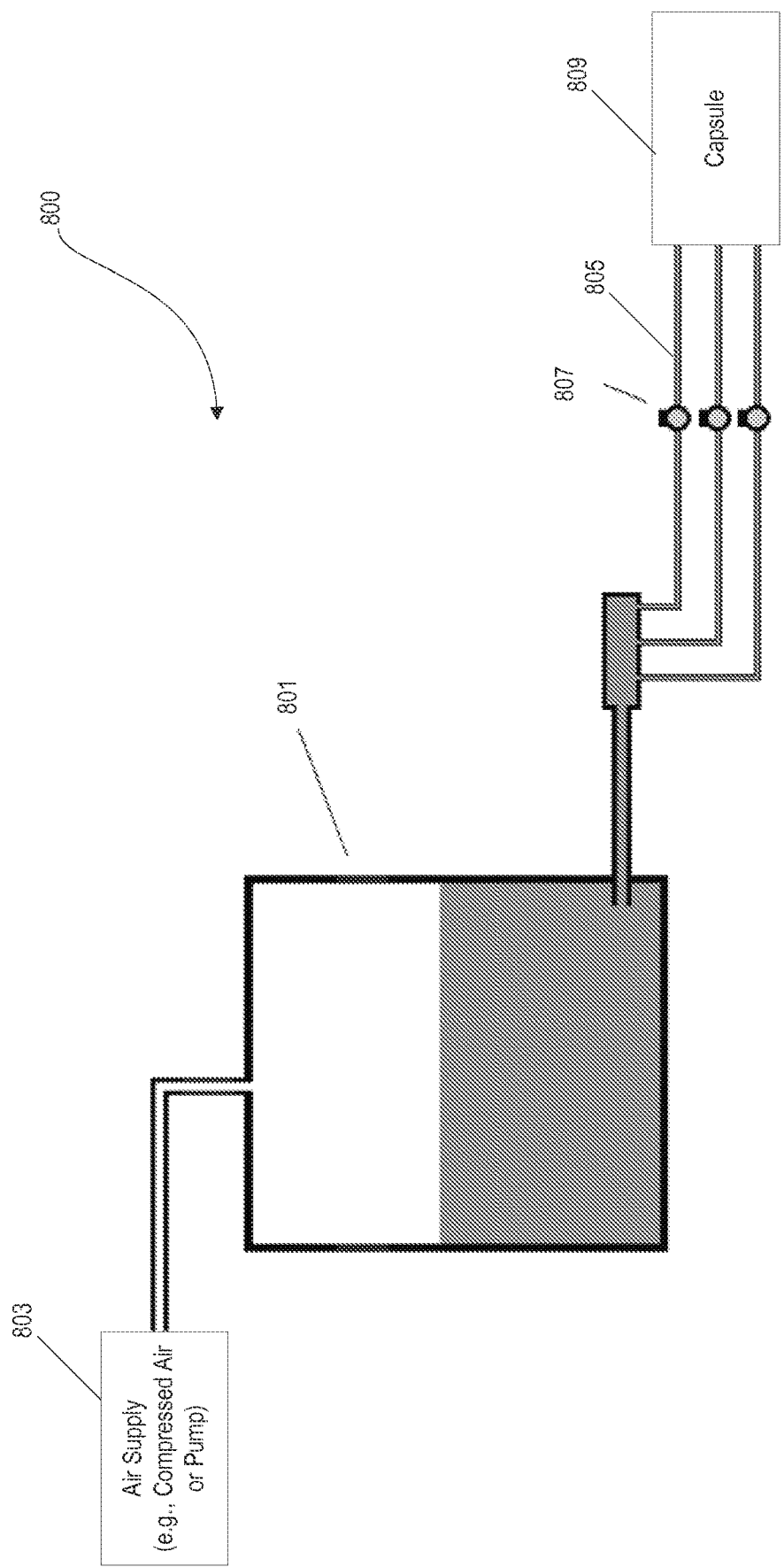
FIG. 8 is a schematic diagram of a pressurized water supply and control system for a hydrojet capsule.

As discussed above, the capsule system receives pressurized fluid from an external system to control lateral movement of the capsule. In the example of FIG. 4, water is drawn from a reservoir/tank 403 by a pump 401. However, other pressurized fluid supply/control mechanisms are possible. FIG. 8 illustrates an example of a fluid distribution system 800 that controllably provides pressurized fluid to each nozzle of the capsule to produce thrust for the capsule. A fluid tank 801 holds water in a pressurized/sealed vessel. An air supply 803 provides pressurized gas/air that is provided to the fluid tank 801 above the held water. The air supply 803 can include, for example, an electrically powered pneumatic pump or a regulated tank of pressurized air. The increased air pressure within the fluid tank 801 applies pressure to the water stored therein and pushes the water into the plurality of supply lines 805. Each supply line is equipped with a controllable pinch valve 807 to regulate the amount of water that passes through each supply line 805 to the capsule 809 and to regulate the flow rate in each supply line 805.

In systems that use a regulated compressed air tank as the air supply 803, the system can have very low power consumption requirements because no electric pump is needed to supply fluid to the capsule. Instead, the compressed gas, which can be carried in portable canisters, is used in conjunction with the dispensing pressure vessel to control maneuvering of the capsule. Because the system does not require electric power to drive a fluid or pneumatic pump, the need for external infrastructure during use is nearly eliminated, making the system more portable and potentially battery powered. These features make the system particularly appealing for use in developing countries and rural areas.

In some embodiments, the fluid distribution system 800 also includes a weight sensor that monitors the weight of the fluid tank 801 in real-time. This weight measurement is then used by the computer control system (e.g., computer 411 in FIG. 4) to estimate the flow rate of the working fluid (e.g., the water in the fluid tank 801) to the capsule 809 and, therefore, the total amount of fluid added to the patient's GI tract. The fluid distribution system then controls the rate at which water is drawn through the suction valve to match the volume of fluid supplied to the patient in order to maintain a net balance between fluid supplied to and removed from the patient.

Figure 9:
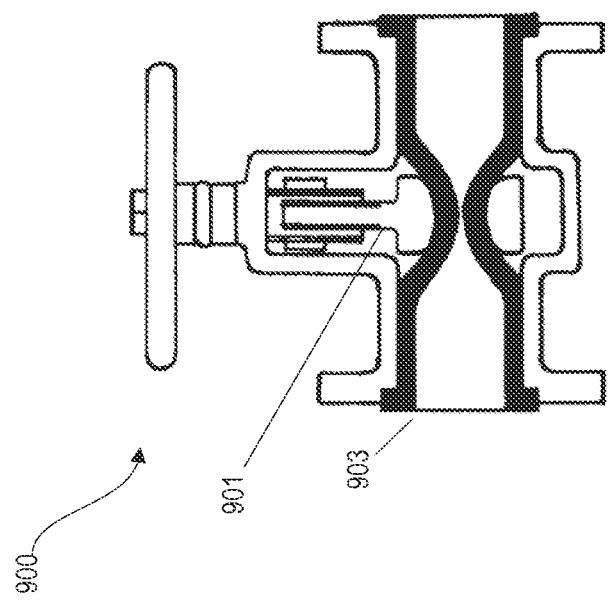
FIG. 9 is a cross-sectional view of a pinch valve for controlling water flow to the hydrojet capsule in the pressurized water supply and control system of FIG. 8.

As discussed above, the rate at which fluid from the supply tank 801 is allowed to enter the fluid supply lines 805 and, ultimately, the rate at which fluid is expelled from each exhaust port of the capsule 809 is controlled by a series of valves 807. FIG. 9 illustrates one example of a controllable pinch valve 900 that can be used in the fluid dispensing system 800 of FIG. 8. The pinch valve includes a controllable piston/actuator 901 that is moved linearly up and down. Downward movement of the piston 901 gradually pinches the supply line 903 to reduce the amount of pressurized fluid that is allowed to move through the supply line 903 and, thereby, controls the rate at which the fluid is expelled from the corresponding exhaust port of the capsule. The piston 901 can be lowered until the supply line 903 is sealed and no fluid is allowed to move through the supply line 903. Among other things, the use of a pinch valve isolates the control mechanism of the valve from water—as such, only safe plastic components contact the water that will be expelled into the body of the patient.

Figure 10:
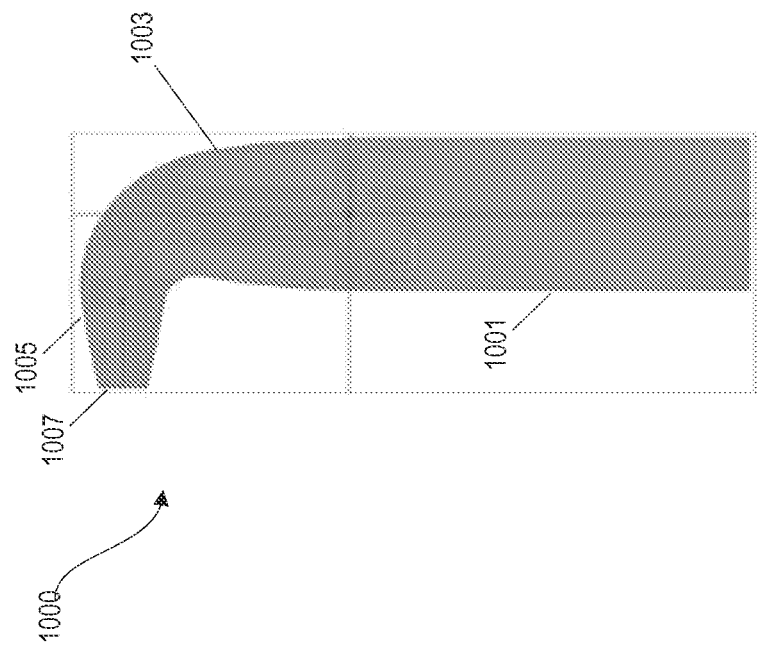
FIG. 10 is a cross-sectional view of a hydrojet for expelling water from a fluid supply line through an exhaust port of a hydrojet capsule.

Finally, FIG. 10 illustrates an example of a jet nozzle 1000 that is equipped on each exhaust port in some embodiments of the capsule system. The main body 1001 of the nozzle/jet is coupled to the distal end of the water supply line and received pressurized water. The diameter of the nozzle body is gradually reduced in an upper portion 1003 of the main body and curves towards an expulsion portion 1005 that is positioned at the exhaust port 1007 of the capsule body. The curved portion 1005 serves to redirect linear flow to be expelled laterally from the capsule body. This flow redirection also results in some forward thrust on the capsule. In other words, the jet design provides both lateral force to move the capsule, as well as forward force tending to push the capsule forward. This features adds to the stability of the capsule overall, as it opposes the lateral jet force much like both extensor and contractor muscles are used to keep a human hand in a stable, well-defined position.

Thus, the invention provides, among other things, an endoscopic capsule system in which lateral movement is controlled by controllably expelling water laterally from the body of the capsule. Some embodiments utilize pressurized gas to provide water pressure creating a very stable water pressure source and a portable system with low power consumption requirements. Some embodiments utilized pinch valves for flow control while ensuring that the fluid that is injected into the body of the patient only contacts safe plastic components. In some embodiments, specially designed jets provide improved thrust for full hemispherical movement. Finally, in some embodiments, the use of an inertial sensor and a video system provide for computer-aided, closed-loop control for a reliable, user-friendly control interface. Various features and advantages of the invention are set forth in the following claims.

What is claimed is:

1. A medical capsule system comprising:
   a capsule housing configured to be inserted into an anatomical structure of a patient;
   a multichannel tether coupled to a rear of the capsule, the multichannel tether including at least one liquid exhaust channel conveying liquid to the capsule housing and at least one suction channel conveying liquid from the capsule housing;
   a plurality of liquid exhaust ports positioned around an outer circumference of the capsule housing each at different surface locations on the capsule housing,
      wherein a normal to the surface location on the capsule housing for each liquid exhaust port of the plurality of liquid exhaust ports is substantially orthogonal to a forward direction of the capsule housing, and
      wherein each liquid exhaust port of the plurality of liquid exhaust ports is configured to controllably expel liquid laterally from a side of the capsule housing to affect lateral movement of the capsule housing; and
   one or more suction ports positioned on the capsule housing and configured to draw liquid into the capsule housing to be conveyed through the at least one suction channel.

2. The medical capsule system of claim 1, wherein each liquid exhaust port of the plurality of liquid exhaust ports includes a controllable valve operable to adjust a rate at which pressurized liquid conveyed through the at least one liquid exhaust channel is expelled from the liquid exhaust port.

3. The medical capsule system of claim 2, wherein the at least one liquid exhaust channel of the multichannel tether includes one liquid exhaust channel, and wherein the controllable valve of each liquid exhaust port of the plurality of liquid exhaust ports is independently controlled to regulate the rate at which the pressurized liquid conveyed through the one liquid exhaust channel is expelled from the liquid exhaust port, and wherein lateral movement of the capsule housing is controlled by simultaneously applying a combination of different rates at which the liquid is expelled from the liquid exhaust ports of the plurality of liquid exhaust ports.

4. The medical capsule system of claim 2, wherein the controllable valve of each liquid exhaust port includes a pinch valve controllable to regulate the flow of liquid through each liquid exhaust port.

5. The medical capsule system of claim 1, further comprising
   an inertial sensor positioned within the capsule housing; and a controller configured to monitor lateral movement of the capsule based on a signal received from the inertial sensor and to regulate lateral movement of the capsule housing by adjusting the rate at which the liquid is expelled through at least one liquid exhaust port of the plurality of liquid exhaust ports based at least in part on the signal from the inertial sensor.

6. The medical capsule system of claim 1, further comprising a controller configured to turn the capsule housing by controlling a rate at which the liquid is expelled through each of the plurality of liquid exhaust ports, wherein controlling the rate at which liquid is expelled includes
expelling the liquid in a first direction at a first flow rate to produce a turning thrust, the first direction being opposite a turning direction of the capsule housing, and
expelling the liquid in a second direction at a second flow rate to dampen the movement of the capsule housing by partially counteracting the turning thrust, the second direction being opposite the first direction and the second flow rate being less than the first flow rate.

7. The medical capsule system of claim 1, further comprising a controller configured to regulate operation of the one or more suction ports to draw liquid from the anatomical structure based at least in part on a rate at which liquid is expelled from each liquid exhaust port of the plurality of liquid exhaust ports.

8. The medical capsule system of claim 1, wherein the capsule housing includes a selectively openable, sealed compartment sized to receive an operational tool, the medical capsule system further comprising the operational tool sized to fit entirely inside the sealed compartment of the capsule housing during use.

9. The medical capsule system of claim 8, wherein the capsule housing is constructed of a disposable material, and wherein the operational tool is reusably positionable in a plurality of disposable capsule housings.

10. The medical capsule system of claim 8, wherein the multichannel tether further includes an operating channel for conveying control signals and data between the operational tool and an external controller when the operational tool is positioned inside the sealed compartment of the capsule housing.

11. The medical capsule system of claim 8, wherein the operational tool includes a video camera system.

12. The medical capsule system of claim 8, further comprising a plurality of operational tools, each configured to perform a different operational function and each sized to interchangeably fit inside the sealed compartment of the capsule housing during use.

13. The medical capsule system of claim 1, further comprising a pressurized liquid system coupled to an end of the multichannel tether opposite the capsule housing, the pressurized liquid system configured to provide pressurized liquid to be conveyed through the at least one liquid exhaust channel of the multichannel tether to the plurality of liquid exhaust ports.

14. The medical capsule system of claim 13, wherein the pressurized liquid system includes a liquid holding tank partially filled with a liquid medium and a pneumatic pressure source configured to increase a pressure of gas above the liquid medium in the liquid holding tank, and wherein the increased pressure of the gas forces the liquid medium through the at least one liquid exhaust channel of the multichannel tether.

15. The medical capsule system of claim 1, wherein the capsule housing does not expel liquid in any direction that provides linear movement of the capsule housing, wherein the multichannel tether includes a flexible, semi-rigid material configured to control linear movement of the capsule housing by pushing and pulling the capsule housing.

16. The medical capsule system of claim 1, wherein the plurality of liquid exhaust ports includes four liquid exhaust ports and the one or more suction ports includes two suction ports,
wherein each liquid exhaust port is positioned at 90° relative to adjacent liquid exhaust ports along the outer circumference of the capsule housing,
wherein each suction port is positioned at 180° relative to the other suction portion along the outer circumference and at 45° relative to adjacent liquid exhaust ports along the outer circumference of the capsule housing.

17. The medical capsule system of claim 1, wherein the one or more suction ports positioned on the capsule includes a plurality of suction ports positioned around the outer circumference of the capsule housing each at different surface locations on the capsule housing, the medical capsule system further comprising a controller configured to turn the capsule housing by
expelling liquid from the capsule housing in a first direction to produce a turning thrust, and
drawing liquid into the capsule housing in a second direction to produce a pulling force in the turning direction.

18. A method of performing esophagogastroduodenoscopy using a hydrojet medical capsule system including a capsule housing, a multichannel tether coupled to a rear of the capsule housing, at least one suction port positioned on the capsule housing, and a plurality of liquid exhaust ports positioned around an outer circumference of the capsule housing each at different surface locations on the capsule housing, wherein a normal to the surface location on the capsule housing for each liquid exhaust port of the plurality of liquid exhaust ports is substantially orthogonal to a forward direction of the capsule housing, wherein the plurality of liquid exhaust ports are configured to controllably expel liquid laterally from a side of the capsule housing at varying rates, and wherein the at least one suction port is configured to draw liquid into the capsule housing, the method comprising:
inserting the capsule housing into an esophagus of a patient through a mouth;
linearly advancing the capsule through the esophagus to a stomach of the patient by applying a pushing force to the multichannel tether, wherein the expelled water does not provide any propulsion in a direction of forward linear movement of the capsule;
providing water to the capsule through at least one liquid exhaust channel positioned within the multichannel tether;
controllably expelling the water through one of the plurality of exhaust ports to affect lateral movement of the capsule;
controllably drawing the water from the stomach through the at least one suction port; and
conveying the water drawn through the at least one suction port from the capsule through at least one suction channel positioned within the multichannel tether.

19. The method of claim 18, wherein controllably expelling water through one of the plurality of exhaust ports to affect lateral movement of the capsule further includes expelling water through one or more exhaust ports to stabilize the capsule and to reduce lateral movement of the capsule.

20. The method of claim 18, further comprising controllably regulating operation of the at least one suction port to draw the water from the stomach based at least in part on a rate at which the water is expelled from the plurality of exhaust ports.

* * * * *